(12) United States Patent
Rein et al.

(10) Patent No.: US 8,657,864 B2
(45) Date of Patent: Feb. 25, 2014

(54) PORTABLE PATIENT TEMPERATURE ADJUSTMENT APPARATUS AND METHOD

(75) Inventors: Erling Bekkestad Rein, Nesoddtangen (NO); Nils Henrik Landeklint, Krakerøy (NO)

(73) Assignee: Otivio AS (NO)

( * ) Notice: Subject to any disclaimer, the term of this patent is extended or adjusted under 35 U.S.C. 154(b) by 464 days.

(21) Appl. No.: 12/335,852

(22) Filed: Dec. 16, 2008

(65) Prior Publication Data

US 2010/0152821 A1    Jun. 17, 2010

(51) Int. Cl.
*A61F 7/00* (2006.01)

(52) U.S. Cl.
USPC ........................................... 607/111

(58) Field of Classification Search
USPC ............ 607/108, 111, 96, 98, 99, 104; 601/9, 601/10, 11, 6, 15, 16
See application file for complete search history.

(56) References Cited

U.S. PATENT DOCUMENTS

| | | |
|---|---|---|
| 1,110,494 A | 9/1914 | Kellogg |
| 1,399,095 A | 12/1921 | Webb |
| 2,113,253 A | 4/1938 | Gray |
| 2,168,611 A | 8/1939 | Thompson |
| 2,626,601 A | 1/1953 | Riley |
| 2,702,552 A | 2/1955 | Moodie |
| 3,094,983 A | 6/1963 | MacLeod |
| 3,217,707 A | 11/1965 | Werding |
| 3,286,711 A | 11/1966 | MacLeod |
| 3,292,613 A | 12/1966 | MacLeod |
| 3,403,673 A | 10/1968 | MacLeod |
| 3,465,748 A | 9/1969 | Kravchenko |
| 3,565,065 A | 2/1971 | Biggs et al. |
| 3,757,806 A | 9/1973 | Bhaskar et al. |
| 3,859,989 A | 1/1975 | Spielberg |
| 3,878,839 A | 4/1975 | Norton et al. |
| 3,896,794 A | 7/1975 | McGrath |
| 3,977,396 A | 8/1976 | Cartier |
| 4,149,529 A | 4/1979 | Copeland et al. |
| 4,186,732 A | 2/1980 | Christoffel |
| 4,269,175 A | 5/1981 | Dillon |

(Continued)

FOREIGN PATENT DOCUMENTS

| | | |
|---|---|---|
| EP | 1884226 A1 | 2/2008 |
| EP | 1929980 A1 | 6/2008 |

(Continued)

OTHER PUBLICATIONS

WIPO, International Search Report dated Jul. 7, 2010 (5 pages) to corresponding International Application No. IB2009/008002.

(Continued)

*Primary Examiner* — Theodore Stigell
*Assistant Examiner* — Brooke Matney
(74) *Attorney, Agent, or Firm* — Fredrikson & Byron, P.A.

(57) ABSTRACT

Embodiments of the invention provide devices and methods for the in situ or in transit adjustment of the core body temperature of a patient. Devices according to some embodiments include a control unit and pressure chamber adapted to apply a pulsating negative pressure to a limb of the patient. An adjustment temperature applied during the application of the pulsating pressure can heat or cool the patient as necessary. Devices and methods disclosed herein can provide for efficient heating and/or cooling of a patient. In addition, devices and methods provide such functionality in a portable device that can be manually carried by an individual.

31 Claims, 14 Drawing Sheets

(56) References Cited

U.S. PATENT DOCUMENTS

| | | | |
|---|---|---|---|
| 4,343,302 A | 8/1982 | Dillon | |
| 4,376,437 A | 3/1983 | Sundheim et al. | |
| 4,648,392 A | 3/1987 | Cartier et al. | |
| 4,945,901 A | 8/1990 | Burcke | |
| 5,063,910 A | 11/1991 | Cartier | |
| 5,074,285 A | 12/1991 | Wright | |
| 5,241,958 A | 9/1993 | Noeldner | |
| 5,300,103 A | 4/1994 | Stempel et al. | |
| 5,358,467 A | 10/1994 | Milstein et al. | |
| 5,425,742 A | 6/1995 | Joy | |
| 2,272,481 A | 11/1997 | Meadow et al. | |
| 5,683,438 A | 11/1997 | Grahn | |
| 5,688,225 A | 11/1997 | Walker | |
| 5,697,920 A | 12/1997 | Gibbons | |
| 6,027,464 A | 2/2000 | Dahlquist | |
| 6,149,674 A | 11/2000 | Borders | |
| 6,277,052 B1 | 8/2001 | Howard | |
| 6,565,593 B2 | 5/2003 | Diana | |
| 6,656,208 B2 | 12/2003 | Grahn et al. | |
| 6,974,442 B2 | 12/2005 | Grahn et al. | |
| 2003/0097163 A1 | 5/2003 | Kane et al. | |
| 2003/0125649 A1 | 7/2003 | McIntosh et al. | |
| 2003/0144690 A1 | 7/2003 | Zheng et al. | |
| 2005/0027218 A1* | 2/2005 | Filtvedt et al. | 601/152 |
| 2005/0137446 A1* | 6/2005 | Rastegar et al. | 600/16 |

FOREIGN PATENT DOCUMENTS

| | | |
|---|---|---|
| FR | 1562252 A | 4/1969 |
| WO | 9840039 | 9/1998 |
| WO | 0180790 | 11/2001 |
| WO | 03045289 | 6/2003 |
| WO | 2004058131 A2 | 8/2004 |

OTHER PUBLICATIONS

English translation of FR1562252, Lecumberry et al.

* cited by examiner

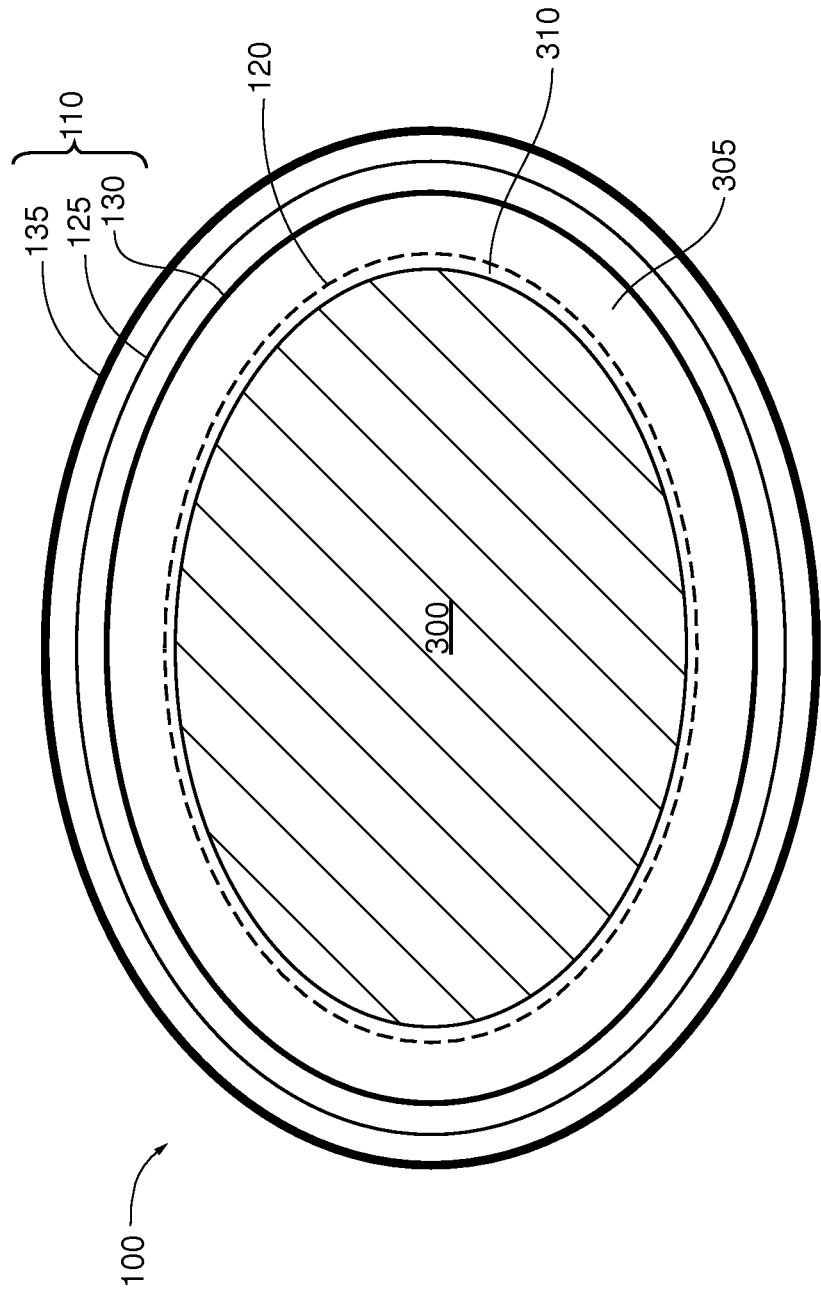

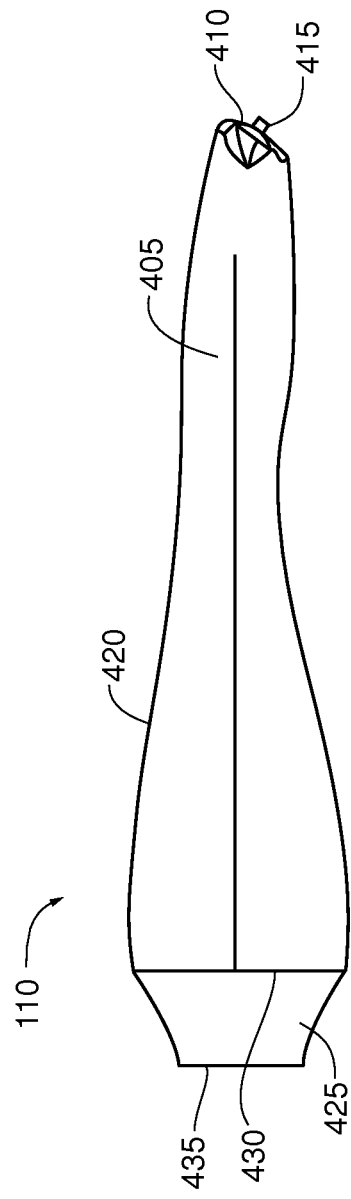

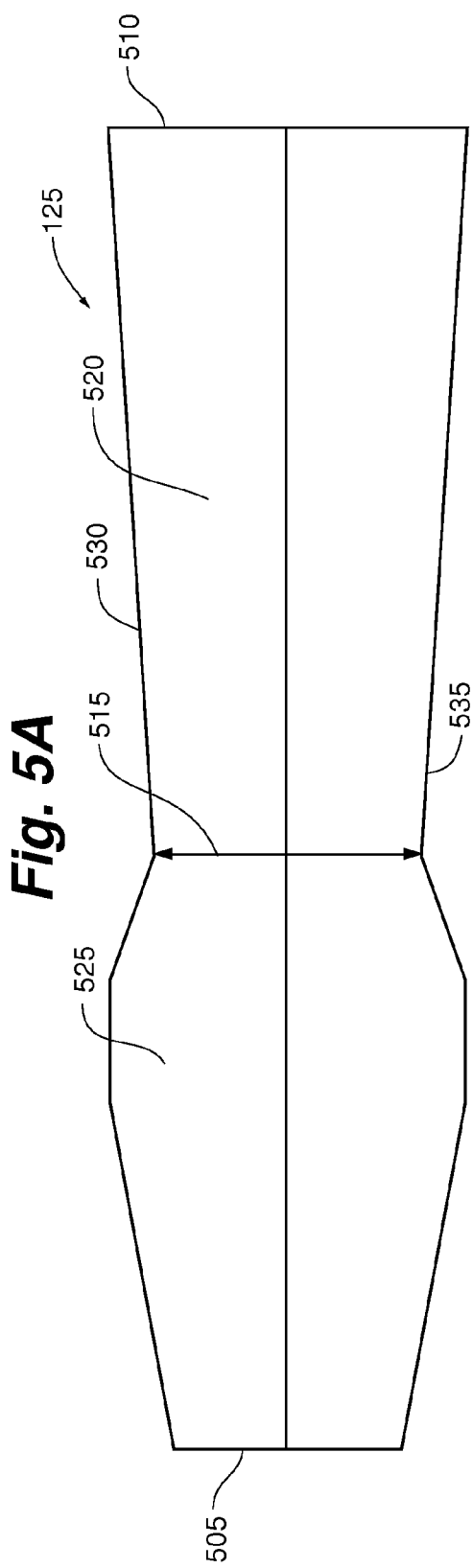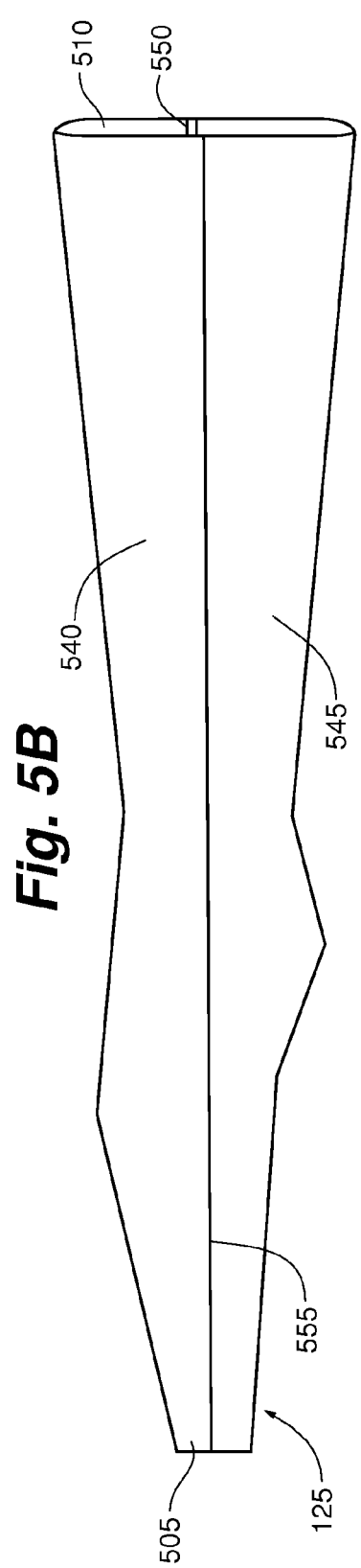

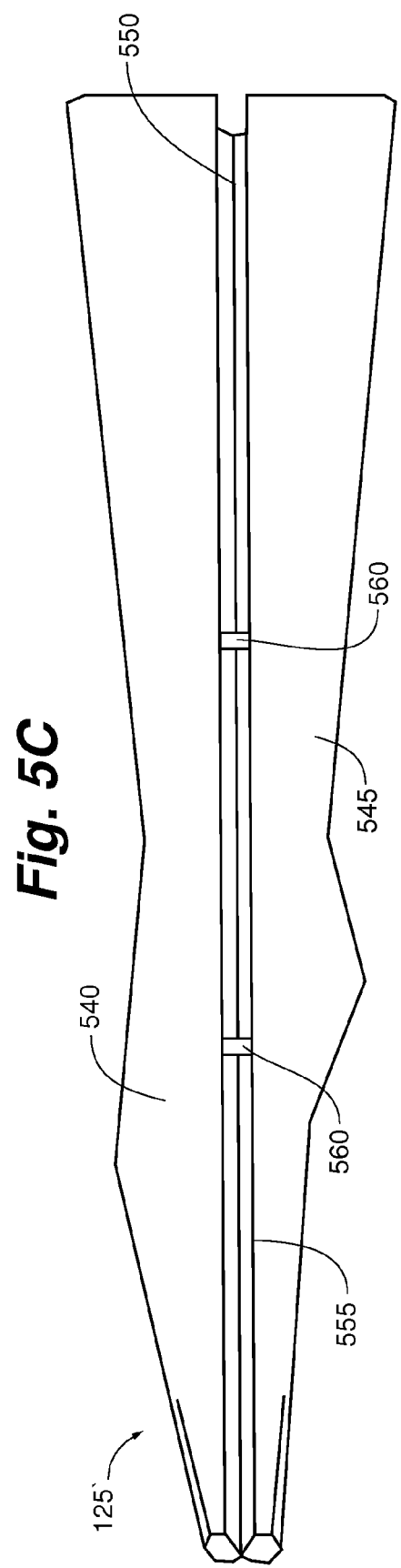

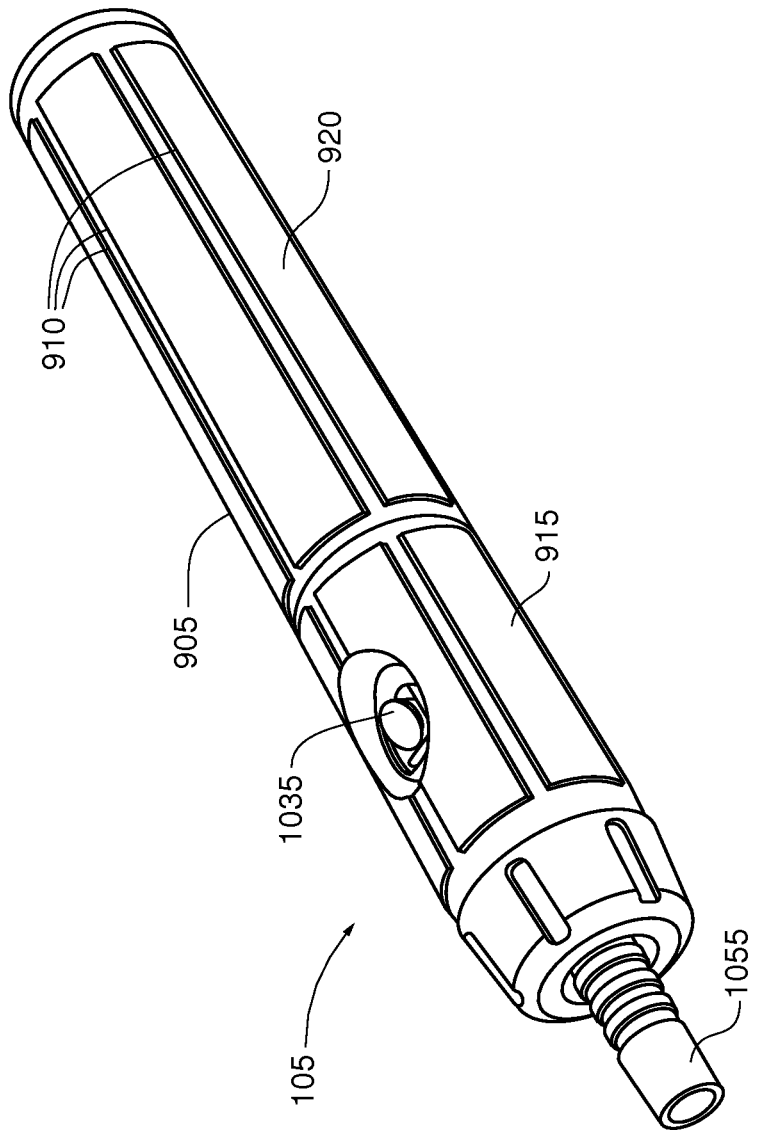

PORTABLE PATIENT TEMPERATURE ADJUSTMENT APPARATUS AND METHOD

TECHNICAL FIELD

The present specification relates to a device for adjusting the core body temperature of a patient. More specifically, portable devices and methods for adjusting the core body temperature of a patient are disclosed.

BACKGROUND

The application of pressure and/or thermal energy is often used to treat various medical conditions.

For example, the combined application of pressure and temperature is taught in U.S. Pat. No. 5,074,285 for the treatment of sporting injuries such as bruising and muscle stiffness. In that system, thermal sources, which could be hot or cold, are introduced into pockets close to the wearer's skin and pressure is applied to a series of air pockets arranged along the limb that are designed to apply a pressure-gradient repeatedly to the limb.

Hypothermia is a condition resulting from a drop in body temperature and varies in degree according to the amount of undercooling. Many methods for treating hypothermia are already known. Generally, these comprise introducing heat into the core of the body by some means to raise the body temperature. Simple treatments can take the form of a warm drink. Sometimes warm air is blown around the body via air blankets.

One of the first physiological responses of hypothermia is peripheral vasoconstriction which reduces the amount of blood at the periphery of the body. This can make it difficult to introduce heat into the body through the application of heat to the body surface. It is known that vessels, including capillaries, arterioles, arteries, venules and veins, can be made to vasodilate under conditions of negative pressure. Vasodilated skin regions, particularly on the forearm, can make efficient heat transfer surfaces.

One system that applies negative pressure to a limb to reduce peripheral vasoconstriction whilst warming the periphery of the patient to treat hypothermia is taught in U.S. Pat. No. 5,683,438 and sold under the mark Thermostat® by Aquarius Medical Corp. In that system, a limb of the patient is placed in a sealed chamber and the pressure inside the chamber is reduced to a negative pressure of between −20 to −80 mmHg (−2.7 to −10.7 kPa). At the same time, thermal energy is delivered to the surface the limb using a thermal blanket, heat lamp or chemical heating elements. Further developments to this system are described in International Publication No. WO 01/80790 A1.

Recently, the application of a pulsating negative pressure has been found beneficial in the adjustment of a patient's core body temperature. Commonly owned U.S. Patent Application Publication No. 2005/0027218 describes a system for applying a pulsating pressure and adjusting the core body temperature of a patient which utilizes a liquid reservoir to effectuate heat and pressure transfer to a limb of the patient. Such application is herein incorporated in its entirety.

SUMMARY

Embodiments of the invention provide devices and methods for the in situ or in transit adjustment of the core body temperature of a patient. Devices according to some embodiments include a control unit and pressure chamber adapted to apply a pulsating negative pressure to a limb of the patient. An adjustment temperature applied during the application of the pulsating pressure can heat or cool the patient as necessary.

In a first aspect, the invention features a portable device for in situ or in transit adjustment of a core body temperature of a patient. The device includes a thermal transfer sleeve, a pressure chamber, and a control unit. The thermal transfer sleeve may be adapted to receive a limb of the patient. The pressure chamber may include a substantially rigid casing for receiving the limb and thermal transfer sleeve, and a heat transfer element for applying an adjustment temperature within the casing. The control unit may be connectable to the pressure chamber and adapted, when connected to the pressure chamber, to alternatingly introduce and release a negative pressure within the pressure chamber. Components of the device, including the thermal transfer sleeve, pressure chamber, and control unit may be configured to fit within a carrying case such that the portable device and the carrying case can be manually carried by an individual.

According to another aspect, in some devices, the thermal transfer sleeve may be adapted to receive a limb of the patient and to be wetted such that the thermal transfer sleeve is in contact with the surface of the limb and air between the thermal transfer sleeve and the limb is minimized. In such case, when the limb and thermal transfer sleeve are inserted into the pressure chamber substantially all of any liquid within the pressure chamber may be carried by the thermal transfer sleeve.

According to another aspect of the invention, the portable device for in situ or in transit adjustment of a patient's core body temperature includes a portable pressure chamber, thermal transfer means, temperature adjustment means, and pressure application means. The thermal transfer means may be adapted for receiving the limb of the patient, facilitating insertion of the limb into the portable pressure chamber, and, when inserted into the portable pressure chamber with the limb, carrying substantially all of any liquid within the portable pressure chamber. The temperature adjustment means may be adapted for applying an adjustment temperature to the thermal transfer means and thereby to the limb when the thermal transfer means and the limb are inserted into the portable pressure chamber. And the pressure application means may be adapted to alternatingly introduce a negative pressure within the portable pressure chamber and release the negative pressure from the portable pressure chamber.

In another aspect, a method for in situ or in transit adjustment of a patient's core body temperature is provided. The method can include installing an absorbent sleeve the patient's limb. The sleeve may be wetted with a liquid. The limb having the wetted sleeve installed thereon, may be inserted into a pressure chamber such that the limb is substantially sealed from external conditions and substantially all liquid in the interior of the pressure chamber is carried by the sleeve. A heating/cooling element within the pressure chamber may be activated to selectively heat or cool the limb. And, a negative pressure may be alternatingly introduced to and released from the pressure chamber.

Methods according to some aspects of the invention can be carried out to effectuate the in situ or in transit adjustment the core body temperature of an unconscious patient. In such cases, the methods can include the additional steps of installing the thermal transfer sleeve about a limb of the unconscious patient, and preparing the limb for insertion into the pressure chamber.

In addition, methods according to some aspects of the invention can include the step of manually carrying a portable device in a carrying case to the patient. Such methods can further include removing the portable device from the carrying case, and checking that the control unit is in fluid connection with the pressure chamber and if not, connecting the control unit with the pressure chamber.

In some embodiments, devices and methods disclosed herein may provide for efficient heating and/or cooling of a patient. Devices and methods may further provide for the application of pulsating pressure to the limb of a patient. Some embodiments may provide such functionality in a portable device that can be manually carried by an individual. In some embodiments, the temperature adjustment devices and methods may be usable in situ or in transit. Such devices and methods may provide for use under environmental conditions. For example, some devices may provide for closed-system operation. Devices and methods may be used without the need for a reservoir of liquid or liquid supply system.

Related technology is disclosed in commonly owned U.S. patent application Ser. No. 12/335,918, filed on Dec. 16, 2008 and titled Portable Patient Temperature Adjustment Apparatus and Method, the entirety of which is hereby incorporated by reference herein.

BRIEF DESCRIPTION OF THE DRAWINGS

The following drawings are illustrative of particular embodiments of the invention and therefore do not limit the scope of the invention. The drawings are not to scale (unless so stated) and are intended for use in conjunction with the explanations in the following detailed description. Embodiments of the invention will hereinafter be described in conjunction with the appended drawings, wherein like numerals denote like elements.

FIG. 3 is a cross-sectional view of an embodiment installed about a limb of a patient.

FIG. 4 is a side plan view of a pressure chamber according to some embodiments.

FIG. 5A is a top plan view of a casing according to some embodiments.

FIG. 5B is a side plan view of the casing of FIG. 5A.

FIG. 5C is a side plan view of an expandable casing according to some embodiments, the casing having been expanded.

FIG. 9 is a perspective view of a control unit according to some embodiments.

DETAILED DESCRIPTION OF ILLUSTRATIVE EMBODIMENTS

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1:
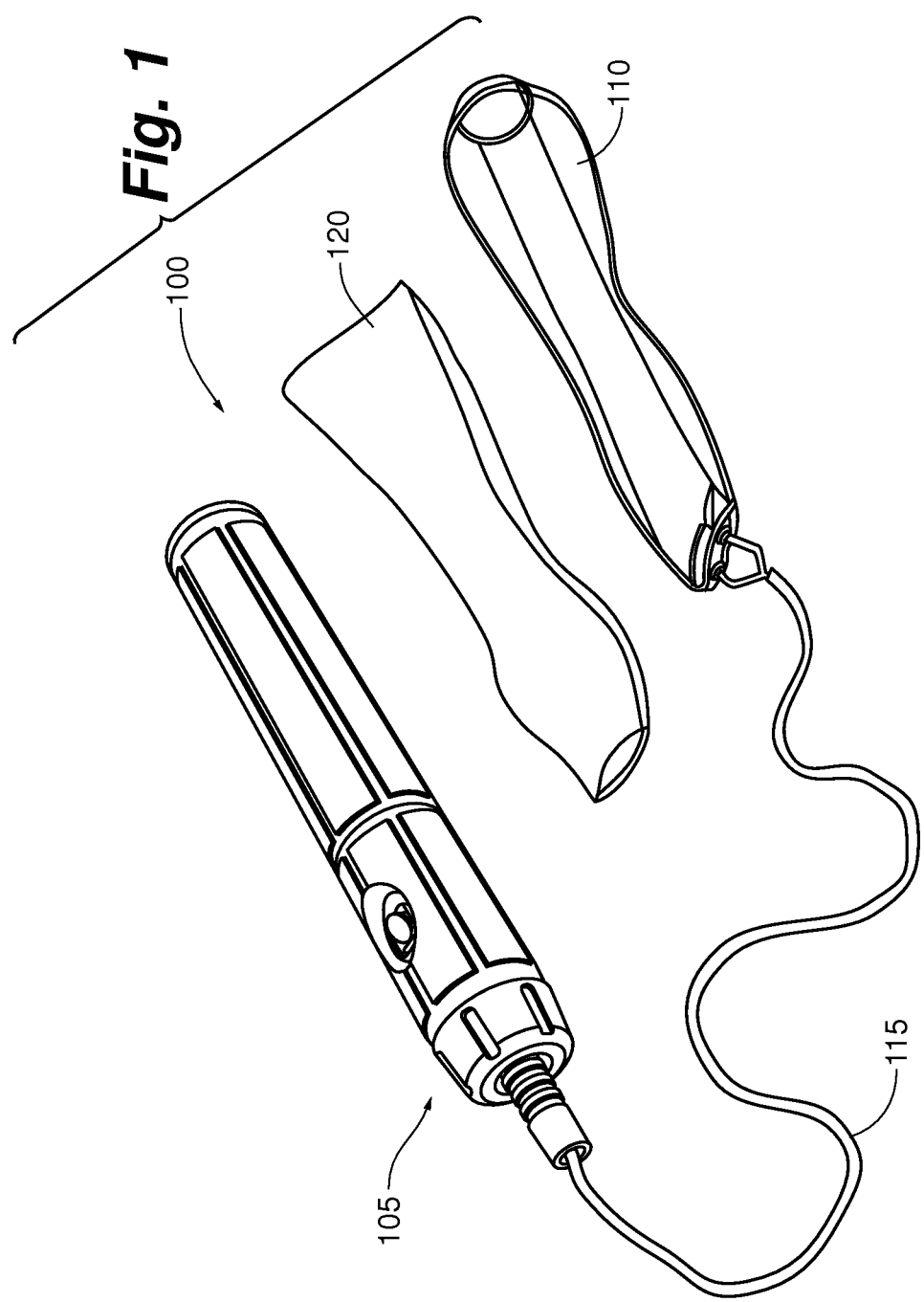
FIG. 1 is a perspective view of a device according to one embodiment.

FIG. 1 shows a portable device 100 for adjusting the core body temperature of a patient according to some embodiments. Devices according to embodiments of the invention adjust the patient's core body temperature through the application of an adjustment temperature while applying a pulsating pressure to the patient's limb. The portable device 100 includes a control unit 105 connected to a pressure chamber 110 via connector 115. The device 100 further includes a thermal transfer sleeve 120 adapted to be installed about a limb of the patient. The pressure chamber 110 is adapted to receive the patient's limb having the thermal transfer sleeve 120 installed thereon. An adjustment temperature can be applied by temperature adjustment means within the pressure chamber 110 to cause heat transfer to or from the limb through the thermal transfer sleeve 120. Contemporaneously, the control unit 105 can apply a pulsating pressure within the pressure chamber 110 via connector 115 to increase blood flow within the limb. Due to the increased blood flow at the point of application of adjustment temperature, the core body temperature of the patient can be effectively adjusted.

Potential uses for the devices and methods described herein take advantage of the improved heating and cooling capabilities provided by the increased blood flow. For example, devices and methods according to some embodiments can be used in connection with any of the important clinical problems listed below:

Prevention of hypothermia by heat transfer to the body (heat gain)
Treatment of hypothermia by heat transfer to the body (heat gain)
Prevention of hyperthermia by heat transfer from the body (heat loss)
Treatment of hyperthermia by heat transfer from the body (heat loss)
To induce hypothermia to treat stroke patients, heart attack and other ischemic diseases, for neurosurgery etc.
To induce hyperthermia to treat cancer patients globally and locally
Changing the pharmacological distribution of drugs systemically and locally because of locally changed blood flow and possibly diffusion
Increasing the distribution of contrast fluid to a local part of the body
Increasing venous circulation
Increasing lymphatic circulation
Promoting healing of tissues by increased blood flow
Increasing antigen-antibody contact through increased blood flow, lymphatic flow and diffusion
Increased flow of substances between vessels and cells through increased diffusion
Reducing fever in patients with neurological injury
Preheating of skin and increase in blood circulation to ease insertion of needles (veneflon) in subcutaneous veins
Increasing blood circulation in ischemic limb
Delivering antibiotics to ischemic limb
Reducing oedema in ischemic limb Moreover, devices according to some embodiments can be especially useful due to their portability. More specifically, rather than requiring a patient needing temperature adjustment to be first moved to a controlled environment, portable temperature adjustment systems and methods such as those described herein allow for the adjustment of the patient's core body temperature where the patient is located (in situ) or as the patient is being transported (in transit). In many situations, timing is critical and the quicker the patients core body temperature can be adjusted, the more likely a positive result for the patient. For example, using devices and methods of the present invention, an unconscious, hypothermic patient can be warmed in the location where the patient is found, rather than delaying treatment until after the patient has been transported. Thus, embodiments of the device can be especially useful in connection with, for example, search and rescue, military, or emergency medicine endeavors.

Figure 2:
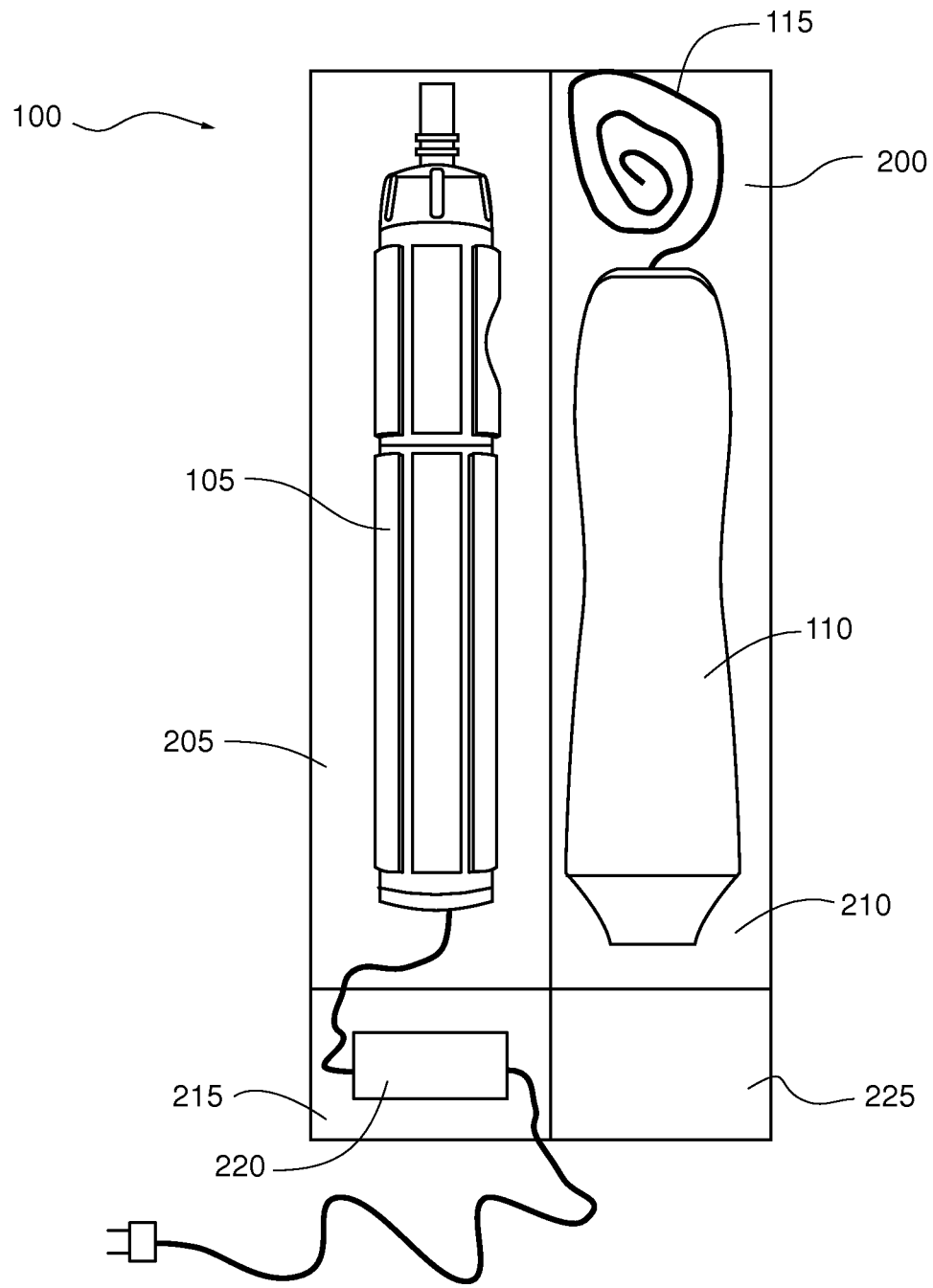
FIG. 2 is a top plan view of a device including a carrying case according to some embodiments.

Various features of embodiments of the present invention render the devices disclosed herein particularly effective for in situ or in transit temperature adjustment. Primarily, the dimensions of the device provide for portability. As shown in FIG. 2 devices according to the present invention are configured to fit within a carrying case 200 such that the portable device and the carrying case are configured to be manually carried by an individual. For example, the carrying case and device can be hand-carried or carried over the shoulder. A carrying case 200 can generally comprise a bag, or rigid case formed to receive the component parts of the device 100. In this view, the carrying case 200 has been opened to reveal various compartments of the case. This particular embodiment includes four compartments: a first compartment 205 configured to receive the control unit 105, a second compartment 210 configured to receive the pressure chamber 110 and connector 115, a third compartment 215 configured to receive a power supply/adapter 225, and a fourth compartment 220 for holding additional items, for example, pre-wet thermal transfer sleeves, a container of liquid, or medical supplies. Moreover, a carrying case can include additional features to facilitate portability such as, for example, a power outlet. A carrying case including an external power adapter can provide for charging or pre-warming of the device while it is still located within the carrying case. For example, a case can include an AC adapter which can be plugged into a standard electrical outlet, or a charger adapted for use with a DC power source such as a 12 V DC vehicle power socket. Of course, one can appreciate that many other cases can be used to carry devices according to the present invention and the specific example shown here should not be construed to limit the invention. Further, in some embodiments various components can be sized such that they are configured to fit within other components of the device. For example, the control unit can be sized so as to fit within the pressure chamber. In addition the carrying case 200 may include one or more straps, a handle, or other features to facilitate manual carrying.

With reference to FIG. 1, devices according to some embodiments can be used by first installing the thermal transfer sleeve 120 and pressure chamber 110 about the limb of a patient. To do so, patient's limb is first inserted into the thermal transfer sleeve 120. Then, the limb having the thermal transfer sleeve installed thereon, is inserted into the pressure chamber 110. Installation of some embodiments including additional steps and features will be discussed in greater detail below.

FIG. 3 shows a cross-section of a patient's limb 300 having a portion of a device 100 according to some embodiments of the invention installed thereon. From the surface of the limb 300 outward, the device 100 includes thermal transfer sleeve 120 and pressure chamber 110. Pressure chamber 110 generally comprises a substantially rigid casing 125 having a heat transfer element 130 installed therein. Further, some embodiments include an outer shell 135 about an outer surface of the casing 125. The pressure chamber 110 is formed to receive the patient's limb 300 within an interior cavity 305 of the chamber. The casing 125 provides the shape of the pressure chamber and generally defines the interior cavity 305. In addition, the casing 125 should be sized to accommodate the heat transfer element 130 within the interior cavity 305. When installed, the pressure chamber 110 provides a substantially fixed volume about the limb 300 having the thermal transfer sleeve 120 installed thereon such that a negative pressure can be generated, preferably within sleeve-chamber gap 305, and the adjustment temperature can be applied within the chamber. In some embodiments, the limb-sleeve gap 310 is small such that air between the thermal transfer sleeve 120 and limb 300 is minimized. Preferably the thermal transfer sleeve 120 is in skin-tight contact with the limb 300. In some embodiments, a constant or intermittent negative pressure is applied within the limb-sleeve gap to evacuate potential air within this gap and to maximize skin-sleeve contact. In such case, the sleeve can include an airtight outer surface. In contrast, sleeve-chamber gap 305 is generally larger than the limb-sleeve gap 310. This is because, in some embodiments, negative pressure is applied within the sleeve-chamber gap 305 and a larger gap is necessary to facilitate air removal from within the gap.

The limb 300 can be any part of a human or animal body that can be easily introduced into the device. For example, a limb can comprise an arm or leg, a portion of an arm or leg (e.g. forearm, hand, lower leg, or foot), or more than one of such parts of the body. In certain situations it may be preferable to use more than one device to increase the amount of heat transfer. For transferring thermal energy to or from the patient, generally the greater the surface area of skin contacted by the thermal transfer sleeve 120 and heat transfer element 130 of the pressure chamber 110, the better. In addition, some areas of skin are generally more efficient at transferring thermal energy from or to the patient's blood, and hence the core of the patient. Some embodiments are preferably installed on the patient's forearm because it provides a large, efficient surface area for heat transfer. Moreover, in comparison with the leg, there is generally less reflex constriction in the forearm, leading to improved thermal energy transfer. Where maximum heat transfer is required, the device should be large enough to accommodate the whole arm or at least as far up the upper arm as possible, e.g., the middle of the upper arm. Engaging the patient's arm above the elbow can maximize the surface area of skin in contact with the thermal transfer sleeve and can also provide for a longer period of blood flow in the distended venous plexus in close proximity to the thermal transfer sleeve. In this way therefore, the volume of blood subject to heat transfer from the heat transfer element of the pressure chamber can be maximized. Moreover, engaging the limb as far up the limb as possible reduces the area of the limb exposed to the external conditions, thus reducing environmental effects which could counter the patient temperature adjustment. In particular, the area of the limb which includes veins nearest the skin can be covered.

Another problem addressed by engaging a large portion of the limb is the counter-current effect present in many mammals. The counter-current effect is a mechanism wherein arteries delivering blood flow to a patient's limb run alongside veins delivering blood from the limb. Heat transfer between the arteries and veins causes the temperature of blood flow within the associated vessels to equilibrate. Thus, venous blood flow is heated or cooled by arterial blood flow, which is at or nearer to the patient's core body temperature, prior to returning to the patient's core. Where the venous blood flow has been temperature adjusted, e.g. by the devices described herein, the heat transfer from the arterial blood flow counteracts the desired effect of the temperature adjustment by drawing the venous blood flow closer to the (undesired) core body temperature. Embodiments of the invention can address this counter-current effect by applying the adjustment temperature to a region of the limb where the counter-current effect is taking place, thus mitigating the heat loss or gain of the venous blood flow due to arterial heat transfer.

However, in the interest of maintaining portability of the device, the pressure chamber and thermal transfer sleeve may be sized so as to accommodate a smaller portion of the limb. For example, a smaller device, in which the proximal end of the pressure chamber engages the arm at or slightly below the elbow around the patient's forearm or biceps and triceps can be easier to install about a patient, especially in situ or in transit.

FIG. 4 shows a perspective view of a pressure chamber 110 according to some embodiments. The pressure chamber 110 can comprise any shape capable of receiving the limb, but it is preferably tubular and of circular or oval cross-section. Cylindrical chambers provide a rounded surface well suited to withstand negative pressures and which generally conforms to limbs. Here, the pressure chamber 110 comprises an elongate cylinder having a curved side wall 405 and an end wall 410. In some embodiments, the pressure chamber includes additional anatomical features to generally conform to the limb. Anatomical features can decrease the interior chamber volume, which in turn minimizes the volume of air which must be displaced from the chamber to provide the negative pressure. Thus, a smaller pump can be utilized with such embodiments. In addition, the provision of such features can reduce the size of the pressure chamber, thus making the device easier to transport. The embodiment of FIG. 4 includes anatomical features to generally conform to an arm. Additionally, the pressure chamber 110 includes a connection 415 located within the end wall 410 for connecting the pressure chamber 110 to a control unit. While the connection 415 can be located generally anywhere on the device, positioning the connection 415 in the end wall 410 can allow for easy access no matter the situation in which the portable device is utilized.

The pressure chamber 110 of FIG. 4 further comprises an outer shell 420 fitted about an exterior surface of the casing. In some embodiments, the outer shell 420 can comprise a substantially elastic material, such as, e.g. Neoprene. An elastic outer shell can be used to bias an expandable casing closed, yet stretch to allow for expansion of the casing to facilitate insertion or removal of the limb. Moreover, an outer shell can act as an insulation layer about the pressure chamber to insulate the chamber interior from external conditions. Such an insulation layer can be especially important given the portability of some embodiments. Because the portable device can be used for in situ or in transit temperature adjustment, the user will often need to use the device where environmental conditions would counteract the operation of the device, e.g. warming a patient in a cold environment. An insulation layer can inhibit negative environmental thermal effects and thus improve performance of the temperature adjustment system.

FIG. 5A shows a casing 125 according to some embodiments. The casing provides the structure for the pressure chamber and defines the interior cavity. Casing 125 comprises an elongate rigid tube having a distal end wall 505 and an open proximal end 510. A patient's limb can be inserted in through the opening in the proximal end 510. In the embodiment of FIG. 5A, the casing 125 is anatomically formed to substantially conform with an arm. The casing 125 includes a wrist portion 515 between wider forearm and hand portions 520, 525. Ideally, the anatomical features of the device are perfectly dimensioned for the limb of the patient, however such practice is impractical given the variety of sizes of patients. Thus, in some embodiments, the anatomical features are provided based upon general population biometrics. In some embodiments, a system for use in the military can comprise a casing formed according to military biometrics so as to fit 95% of U.S. soldiers. FIGS. 5A and 5B include exemplary dimensions formed according to such statistics.

Further, in some embodiments, the casing 125 is expandable. An expandable casing can facilitate installation of the casing about the patient's limb. Installation of a pressure chamber including some anatomical features, for example the wrist portion 515 of FIG. 5A, can be difficult because the patient must maneuver his or her limb or a portion thereof to get past the feature. Moreover, proper installation of a pressure chamber about the limb of an unconscious or injured patient can be hindered due to the patient's inability to maneuver his or her limb past the anatomical features. With an expandable casing, many of these problems can be overcome. In some embodiments, an expandable casing comprises a casing having a hinged edge 530 and opposed openable edge 535. FIG. 5B shows a side view of the casing 125 of FIG. 5A along the openable edge 535. The casing can be expanded by pivoting the top half 540 of the casing relative to the bottom half 545 of the casing about hinge 550 on the opposite edge of the casing, causing the casing to split along fissure 555. As the casing 125 splits, the cross-sectional dimension of the casing expands, facilitating insertion of the limb. A side plan view of an expanded casing 125' is shown in FIG. 5C. In this view, the top and bottom halves 540,545 of the casing have been separated along fissure 555 by pivoting about hinge 550. Alignment members 560 are shown extending between the top and bottom halves 540, 545 so as to maintain alignment of the halves 540, 545. Alignment members 560 can be rigid protrusions extending from the top or bottom half 540, 545 of the casing into receiving members on the opposite half. When the casing 125' is expanded, such as in FIG. 5C or during installation or removal of a limb, alignment members 560 prevent misalignment of the casing. Of course, one of ordinary skill in the art can appreciate that there are many additional ways to maintain proper alignment, all of which should be considered as within the scope of this invention.

In some embodiments, to further facilitate portability of the device, the casing may be capable of being disassembled, e.g. it may break in half, for example along a fissure around the entire casing. Each separate piece or half of the can then be easily stowed within a carrying case while taking up minimal space. In use, each separate piece of such a casing can be removed from the carrying case and fitted together to form the casing. Other components of the pressure chamber, e.g. heat transfer element and outer shell, can then be installed within or about the assembled casing.

Referring back to FIG. 3, pressure chambers 110 according to some embodiments further comprise a heat transfer element 130 adapted to facilitate heat transfer within the pressure chamber 110 so as to apply an adjustment temperature to the limb 300, via the thermal transfer sleeve 120. Embodiments of the device can be used for warming, cooling, or both warming and cooling of a patient's core body temperature. When the device is used to warm a patient, the heat transfer element facilitates heat transfer to the limb and the adjustment temperature can be said to be a warming temperature. When the device is used to cool a patient, the heat transfer element facilitates heat transfer from the limb and the adjustment temperature can be said to be a cooling temperature. In either case, heat transfer effectuated by the heat transfer element occurs via the thermal transfer sleeve. The locally applied heat affects the circulation locally. Cool adjustment temperatures can constrict vessels locally, while warm adjustment temperatures tend to dilate vessels. This can sometimes work to the disadvantage of the patient.

Devices according to some embodiments can be adapted to provide a warming, a cooling, or both a warming and a cooling adjustment temperature. In some embodiments, a user of the device can tune the adjustment temperature to any desired level within an operating range. Conversely, in some embodiments, the adjustment temperature is restricted to a preset value or one of a few selected predetermined values. A warming adjustment temperature should be selected so as to be at or above the current core body temperature of the patient. Generally, the selected warming temperature is at or above the normal physiologic temperature of the patient. Of course, in some applications, the applied warming temperature will be below the normal physiologic temperature of the patient. In cooling applications, the cooling temperature is generally selected to be at or below the normal physiologic temperature of the patient, however, in some applications, the applied cooling temperature will be above the normal physiologic temperature of the patient. In embodiments capable of providing a warming temperature, the device should be configured so as to be capable of applying a temperature of at least about 37.0 degrees Celsius (° C.). Preferably, the warming temperature will be in the range of 37.0° C. to 43.0° C. (e.g. 42.5° C.) at the patient's skin. In embodiments capable of providing a cooling temperature, the device should be configured so as to be capable of applying a temperature of at least below about 24.0° C., and preferably below about 10.0° C. Preferably, where the cooling temperature will be applied to a patient's limb without regional anesthesia, the cooling temperature will be in the range of 22.0° C. to 23.0° C. (e.g. 22.5° C.) at the patient's skin. Where the cooling temperature will be applied to the patient's limb with regional anesthesia, the cooling temperature can be in the range of 4.0° C. to 10.0° C. (preferably about 10.0° C.).

Figure 6:
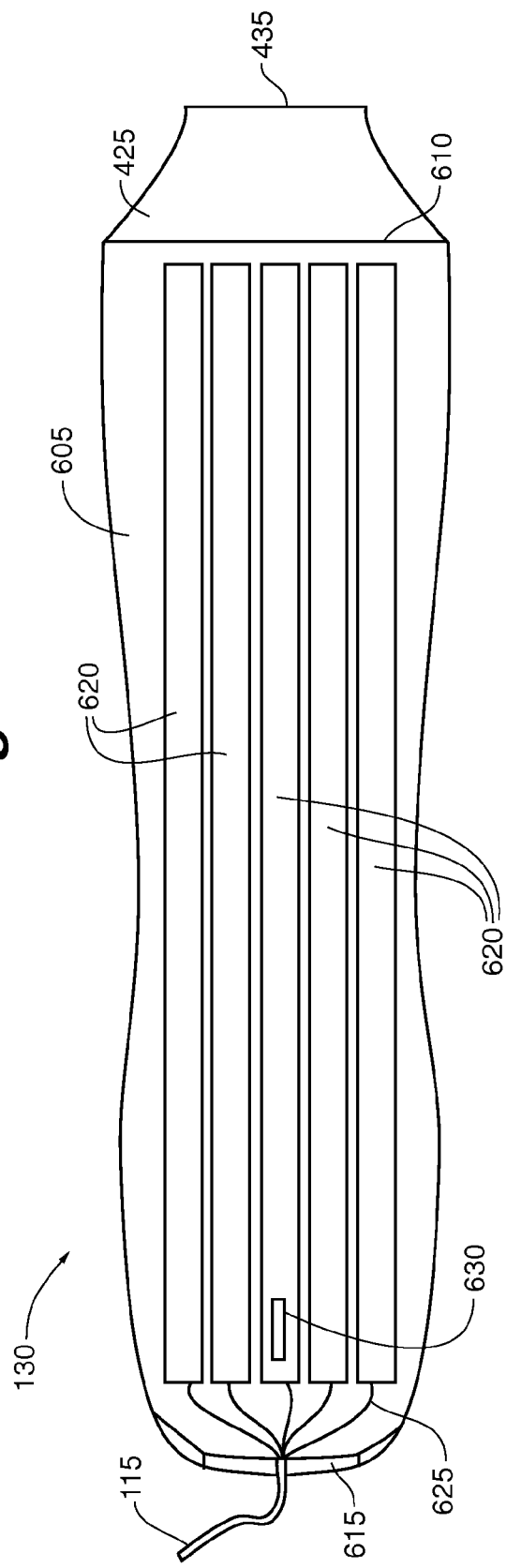
FIG. 6 is a top plan view of a heat transfer element according to some embodiments.

FIG. 6 shows an embodiment of a heat transfer element 130 according to some embodiments. The heat transfer element 130 comprises a tube-like mitten 605 having an open proximal end 610 and a distal end 615 which, in some embodiments, is closed. The mitten 605 can be installed inside the casing of the pressure chamber such that it lines the interior cavity of the chamber. The exemplary heat transfer element 130 shown is shaped to conform with a casing including anatomical features for use with an arm such as that of FIG. 5A. In this view, the heat transfer element 130 has been removed from the pressure chamber. The term "mitten" as used herein should not limit the heat transfer element to embodiments wherein the limb is an arm or hand, rather the term "mitten" should be broadly construed to designate a lining that generally conforms with the casing in which it is installed. Mitten 605 can be rigid, or flexible and can comprise any suitable material. Because the mitten often comes into contact with the limb of the patient and can line the interior of the substantially rigid casing, in some embodiments the mitten comprises a soft or cushioned material, such as, e.g. Neoprene.

Heat transfer element 130 further comprises thermoelectric devices 620 installed within or along a surface of the mitten. The thermoelectric devices 620 are adapted to thermally communicate with the limb via the thermal transfer sleeve when the limb and thermal transfer sleeve are received in the pressure chamber. Thermoelectric devices 620 can comprise any such device capable of effectuating heat transfer under an applied electrical current or potential. The thermoelectric devices can be heating devices, cooling devices, devices capable of both heating and cooling, or a combination of heating and cooling devices. For example, the thermoelectric devices can comprise Peltier devices, resistive heating elements, or cooling fans. In some embodiments, the heat transfer element 130 can be constructed of a material that is itself a resistive heating material, for example, a mesh of resistive threads. Electrical wires 625 connect the thermoelectric devices 620 to thermal control circuitry which is adapted to control the operation of the thermoelectric devices 620. In some embodiments, the thermal control circuitry includes a controller located within the control unit and connected to electrical wires 625 via connector 115. Thermoelectric devices can be located at any location within or about the mitten. In the embodiment of FIG. 6, the thermoelectric devices are regularly dispersed about the entire surface of the mitten. However, in some embodiments, thermoelectric devices are positioned irregularly or located so as to create independent heating/cooling zones within the mitten.

The embodiment of FIG. 6 further includes a temperature sensor 630. Temperature sensor 630 can provide feedback to the thermal control circuitry or temperature control unit so that the desired adjustment temperature within the pressure chamber can be maintained. Some embodiments may include multiple temperature sensors each keyed to independent heating/cooling zones within the pressure chamber so that each zone can be separately controlled. In addition, some embodiments can include additional temperature sensors or the capability to communicate with additional temperatures sensors. For example, some embodiments can include an external or ambient temperature sensor for sensing an ambient temperature and adjusting the applied or available adjustment temperatures based on this reading. Further, some embodiments can include a thermometer or connection to a thermometer which can be separately connected to or used with the patient to provide feedback in the form of a current core body temperature of the patient.

In some embodiments, the pressure chamber further comprises a seal element adapted to seal the pressure chamber about the limb when the limb is received by the pressure chamber. Seal element should provide a substantially air tight seal about the limb so that the negative pressure can be introduced to the pressure chamber and can be applied throughout the negative pressure period. A seal element according to embodiments of the portable device need not perfectly seal the chamber, rather the emphasis of the feature should be on ease of installation about the patient. In some embodiments, the seal element comprises a cuff made of a stretchable, resilient material. Alternatively, the seal element can comprise an inflatable cuff which inflates to engage the limb. An exemplary cuff 425 is shown in FIG. 4. Here, the cuff 425 is attached to the pressure chamber 110 about the open proximal end 430 of the device. Cuff 425 narrows to opening 435, through which the patient's limb can be inserted. When the limb is inserted, the stretchable material of the cuff 425 expands at the opening 435 to accommodate the limb and maintain a seal about the outer surface of the limb. As seen in FIG. 4, a cuff 425 can be joined to outer shell 420 and can comprise the same material as the outer shell or a different material. Alternatively, as shown in FIG. 6, cuff 425 can be connected to the heat transfer element 130. Likewise, the cuff can be connected or attachable to the thermal transfer sleeve. Of course many other seal element designs and connections can be used and should be understood to be within the scope of invention. For example, a cuff extending from the heat transfer element can be connected with a cuff extending from the outer shell to form a single cuff connected to both layers.

In some embodiments, the pressure chamber 110 further includes an extension feature. An extension feature can provide an extensible, semi-rigid portion of the pressure chamber so that the chamber can be extended to cover a larger portion of the limb, which can be desirable in some embodiments as described above. An extension feature can comprise, for example, an accordion feature having a plurality of rigid support members or a coiled rigid support member encased within or coupled to a flexible connection material. The support member maintains the sleeve-chamber gap of the device, and the flexible connection material maintains the seal of the chamber. In some embodiments, an extension feature is included between the open proximal end 430 and the seal element 425 of the pressure chamber 110 so that the pressure chamber 110 can be extended beyond and/or flex with a joint, e.g. an elbow or knee, of the limb. Extension features can be permanently connected to the pressure chamber, or can be removably connected such that the feature can be used only when necessary.

Referring back to FIG. 1, devices according to the present invention further comprise a thermal transfer sleeve 120. Thermal transfer sleeve 120 is installable about the patient's limb and facilitates thermal energy transfer to or from the limb. The incorporation of the thermal transfer sleeve further enables the portability of devices according to the present invention. In previously known devices, large and difficult to transport liquid management systems are often required to supply and regulate the liquid reservoir which the device uses as a heat and pressure transfer medium. In addition, the liquid reservoirs themselves are quite bulky and heavy. As such, devices of the prior art are not readily transportable by an individual. In contrast, embodiments of the present invention do not require or utilize a free flowing volume of liquid within the pressure chamber to effectuate heat and pressure transfer to the limb. Rather, embodiments utilize the thermal transfer sleeve and a small, fixed volume of liquid (or no liquid at all) to perform these functions. Accordingly, by eliminating the use of liquid reservoirs as heat and pressure transfer means, portability is enhanced.

Figure 7:
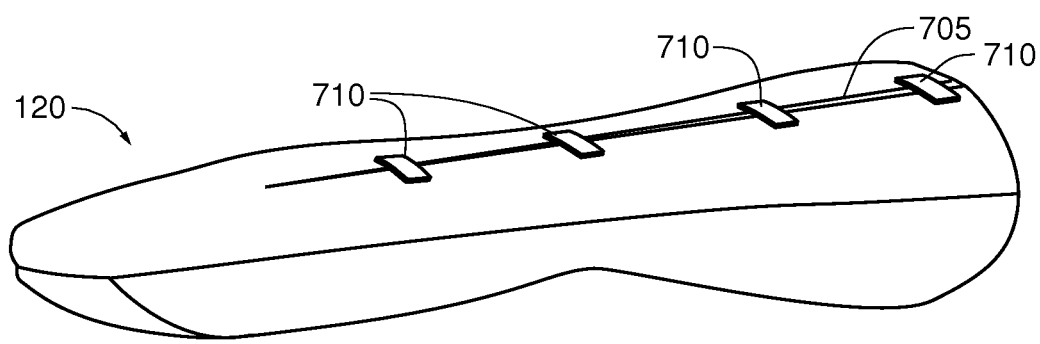
FIG. 7 is a perspective view of a thermal transfer sleeve according to some embodiments.

FIG. 7 shows a perspective view of a thermal transfer sleeve 120 according to some embodiments. The thermal transfer sleeve 120 generally comprises a cloth-like, material formed to receive the patient's limb. In this embodiment, the thermal transfer sleeve 120 is formed to receive an arm. When installed, the thermal transfer sleeve should generally conform to the limb. For example, the thermal transfer sleeve can comprise a stretchable material that can stretch to engage the limb. Moreover, the thermal transfer sleeve can include coatings or layers to afford the sleeve additional properties, for example, a thermal transfer sleeve can include a coating or surface that is airtight, watertight, or both airtight and watertight. In some embodiments, the thermal transfer sleeve 120 comprises a wettable material capable of absorbing and storing a volume of thermally conductive liquid. In such embodiments, when the limb and thermal transfer sleeve are inserted into the pressure chamber substantially all of any liquid within the pressure chamber can be carried by the thermal transfer sleeve. Alternative heat transfer materials, e.g. a thin metallic sheet or a cloth material bearing a thermally conductive coating, are also contemplated and should be construed as within the scope of the invention. Preferably, the thermal transfer sleeve comprises a high-absorbency, wettable material, e.g. synthetic chamois cloth. Wettable materials may be preferred because when installed about a limb and wetted, such materials can adhere to the limb in skin-tight contact. Thus the surface area of the limb contacted by the thermal transfer sleeve is maximized, providing for increased and more uniform heat transfer through the wetted material. In various embodiments, the liquid used to saturate the thermal transfer sleeve is water, however other thermally conductive liquids can be used.

The embodiment of FIG. 7 includes additional features which can facilitate installation and adjustment of the sleeve 120 about a limb. Slit 705 extends along a portion of the sleeve 120 and allows for partial separation of the sleeve to facilitate installation of the thermal transfer sleeve 120 about the limb. Such a feature can be especially useful when the sleeve is being installed about the limb of an unconscious patient. Closing features 710 are provided to secure the sleeve together about the slit 705. Closing features 710 can comprise any suitable connection means such as, for example, hook and loop, snap, adhesive, or another connector. In addition to facilitating installation of the thermal transfer sleeve 120, closing features 710 and slit 705 can be used to adjust the sleeve once installed about the patient's limb. For example, once installed about the limb, opposing sides of the slit 705 can be cinched and closing features 710 reattached so that the sleeve 120 is in close contact with the limb and the limb-sleeve gap is reduced.

In some embodiments, the device can include a pre-wet sleeve. Pre-wet sleeves are provided with the sleeve material already saturated with liquid. By providing the thermal transfer sleeve pre-wet, one or more installation steps can be eschewed. Moreover, the provision of such sleeves prevents the user from having to locate a source of liquid at installation. A pre-wet sleeve can comprise any of the thermal transfer sleeves discussed above, or it may be otherwise constituted. The pre-wet sleeve is typically provided in a liquid-impermeable package so that the sleeve remains wet until use. After use, the pre-wet sleeve may be discarded, or retained for future re-wetting and use. Additionally, in embodiments including a carrying case, a separate compartment for stowing one or more packages of pre-wet sleeves may be provided.

Referring back to FIG. 1, devices according to embodiments of the invention further comprise a control unit 105. The control unit 105 is connectable, e.g. via connector 115, to the pressure chamber 110 and adapted to deliver a pulsating pressure to the pressure chamber 110. In addition, in some embodiments, the control unit 105 regulates the adjustment temperature applied within the pressure chamber 110.

To deliver the pulsating pressure, the control unit 105 can cause air to be delivered to or removed from the pressure chamber. The term "air" used herein as a pressure regulating medium is in no way intended to limit the invention to devices that just use air. Other gases, for example, inert gases, would also be suitable although may add considerably to the cost of operation and the portability of the device. Moreover, unless otherwise noted, any reference to a pressure within this disclosure should be construed as the pressure relative to local atmospheric pressure at the time of use of the device. For example, the term "positive pressure" references a pressure greater than atmospheric pressure. In another example, a pressure of −80 mmHg (−10.7 kPa) within the chamber would correspond with an absolute internal pressure of 680 mmHg (90.7 kPa) based on an atmospheric pressure of 760 mmHg (101.3 kPa). Moreover, any reference to "higher" or "greater" negative pressures should be understood to reference pressures that are more negative than others, i.e. −80 mmHg is a "higher" and a "greater" negative pressure than −60 mmHg.

Devices and methods according to the present invention operate on the premise of the application of a pulsating pressure. A "pulsating pressure," as used herein, refers to the repeated, alternating introduction of two or more different pressures during consecutive time periods. In one example, a pulsating pressure can comprise the alternating introduction of an applied pressure and release of the applied pressure so as to return to approximately atmospheric pressure. The applied pressure can be either a positive pressure or a negative pressure. In embodiments using a negative pressure, the period during which the negative pressure is introduced and is present is referred to as the negative pressure period. Likewise, in systems utilizing a positive pressure, the period during which the positive pressure is introduced and is present is referred to as the positive pressure period. In each case, the period during which the applied pressure is released and atmospheric pressure is returned and is present is referred to as the atmospheric pressure period. Generally embodiments discussed herein are discussed with reference to a negative applied pressure. In most cases negative pressure systems can be readily substituted with positive pressure systems by inverting pump and valve operations or by other adjustments apparent to one of ordinary skill in the art. Thus, one should appreciate that any discussion of negative pressure systems herein, unless otherwise indicated, likewise applies to positive pressure systems. In such case, the term "negative pressure" as used herein should be interchanged with the term "positive pressure" and pressure values should likewise be substituted. Accordingly, the invention should not be construed to exclude devices and methods using a positive pressure rather than a negative pressure.

In some embodiments, multiple, consecutive, alternating negative pressure periods and atmospheric pressure periods are applied to a limb within a pressure chamber without removing the limb from the chamber. The negative and atmospheric pressure periods can be of the same or a different duration. In some embodiments, the negative pressure periods and atmospheric pressure periods can be selected according to known methods, such as those described in commonly owned U.S. Patent Application Publication No. 2005/0027218 which is herein incorporated by reference. For example, in some embodiments the negative pressure period is between 1 second and 20 seconds in duration and the atmospheric pressure period is between 2 seconds and 15 seconds in duration. Further, in some embodiments, the negative pressure period is between 5 seconds and 15 seconds in duration and the atmospheric pressure period is between 5 seconds and 10 seconds in duration. And in some preferred embodiments, the negative pressure period is approximately 10 seconds in duration and the atmospheric pressure period is approximately 7 seconds in duration.

The pressure applied within the pressure chamber can be fixed or selected at the point of use. Embodiments of devices and methods according to the present invention provide for the application of a negative pressure of −80 mmHg (−10.7 kPa) or less. Accordingly, corresponding pressure chambers are configured to withstand negative pressures of at least −80 mmHg (−10.7 kPa), and preferably considerably more. In some embodiments, the negative pressure can be −60 mmHg (−8.0 kPa) or less. Some embodiments utilize a negative pressure of approximately −40 mmHg (−5.3 kPa). The preferred negative pressures have been selected in order to reduce complications that can possibly arise from the application of higher negative pressures. In some embodiments, a negative pressure has been selected to encourage local vasodilation in the surface of the limb while minimizing the risk of possible complications. As described above, pulsating the negative pressure has been found to encourage blood flow and for this reason a pulsating negative pressure of 0 to −40 mmHg (0 to −5.3 kPa) is preferably generated in the chamber.

Figure 8:
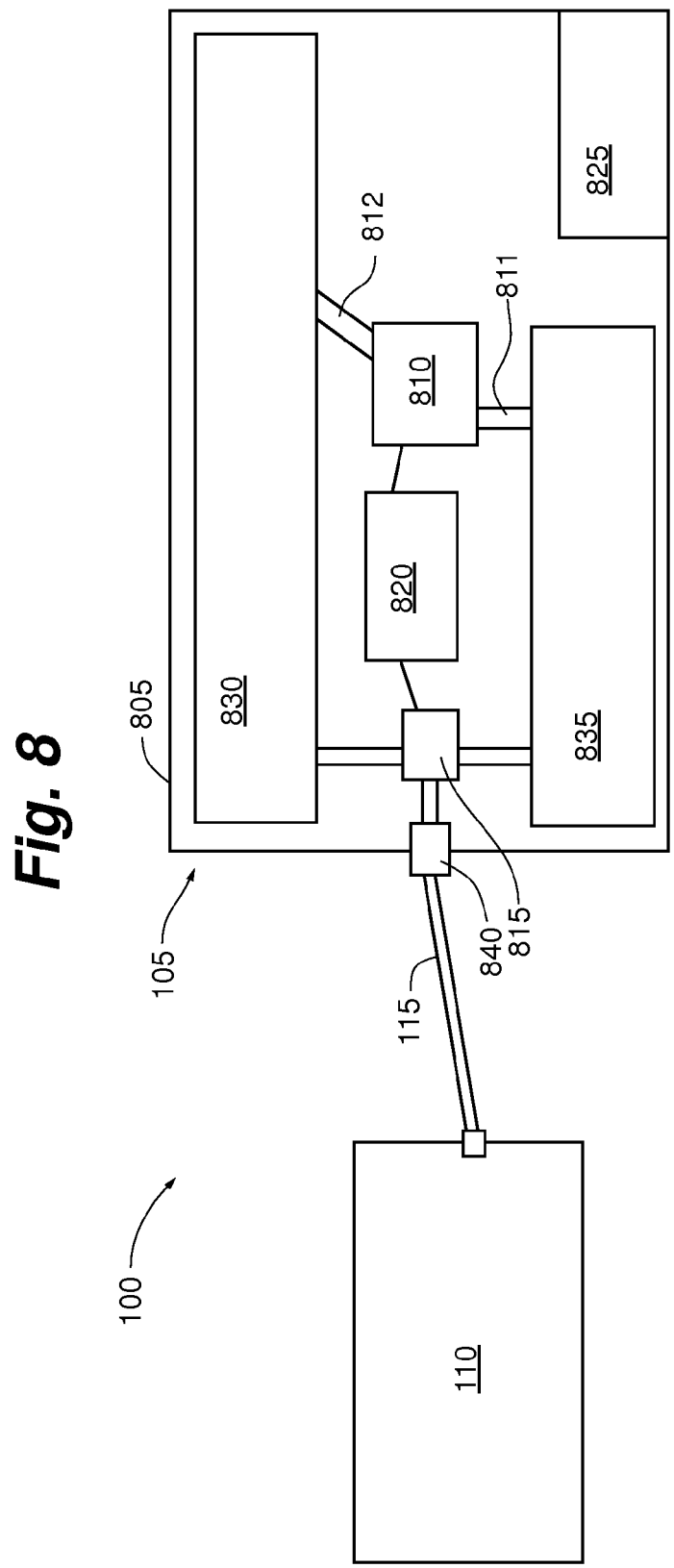
FIG. 8 is a schematic diagram of a control device according to some embodiments.

FIG. 8 is a schematic representation of a device 100 including control unit 105 according to some embodiments. Control unit 105 comprises a portable housing 805 having a pump 810, valve 815, controller 820, and power supply 825 connected thereto. The portable housing 805 further includes first and second chambers 830, 835 and a connector input 840 for providing fluid connection to the pressure chamber 110 via connector 115. First and second chambers 830, 835 can be substantially air impermeable so as to prevent leakage of air into or out of each chamber. Pump 810 includes a pump inlet 811 in fluid connection with the second chamber 835 and a pump outlet 812 in fluid connection with the first chamber 830. Accordingly, the pump 810 is adapted to displace air from the second chamber 835 and deliver the displaced air to the first chamber 830. Valve 815 is adapted to alternatingly connect the connector input 840 (and therefore the pressure chamber 110) with the first chamber 830 and the second chamber 835. Controller 820 is connected with the pump 810 and valve 815 to control the introduction and the release of the negative pressure to and from the pressure chamber 110. The controller 820 can accomplish a pulsating negative pressure within the pressure chamber 110 by setting the valve 815 so that the connector input 840 is in communication with the second chamber 835 (a low pressure source). Air from the (relatively high pressure) pressure chamber is drawn into the second chamber 835 through this connection. To restore the pressure chamber 110 to atmospheric pressure, the controller 820 can switch the valve 815 such that the first chamber 830 and pressure chamber are connected causing the pressures to equilibrate at approximately atmospheric pressure. By repeatedly switching the valve 815, negative pressure pulses can be applied within the pressure chamber 110.

In addition, the controller 820 can comprise the thermal control circuitry for controlling the adjustment temperature within pressure chamber 110. In such case, the controller is provided a connection with the pressure chamber 110 via connector input 840 and connector 115 or an additional connection to the pressure chamber 110. Power supply 825 is connected with the portable housing 805 and adapted to supply power to pump 810, valve 815, controller 820, and, in some embodiments, the heat transfer element within the pressure chamber 110. The power supply enhances the portability of the device 100, allowing for use of the device in remote locations where access to power is limited. Moreover, some embodiments include a power adapter for using the device when a power source is available, or for charging the portable power supply 825.

Connector 115 provides for the connection from the control unit 105 to the pressure chamber 110. The connector 115 can comprise a length of tubing for transferring air to or from the pressure chamber to apply a pulsating pressure therewithin. Additionally, in some embodiments, the connector 115 can provide for an electrical connection from the control unit to the pressure chamber. The electrical connection can deliver power and/or control signals to or from electrical components within the pressure chamber. To provide such connection, electrically conductive wire can be molded into or attached to the tubing or be provided separately from the tubing. In some embodiments, the connector comprises a length of silicon tubing having an electrical lead helically coiled about the tubing and molded or attached thereto. Such a connector can provide a durable, rugged connection between the pressure chamber and the control unit.

FIG. 9 shows a control unit 105 according to some embodiments of the invention. The control unit 105 comprises a portable housing 905 for protecting and holding the components of the control unit. The portable housing 905 can comprise any suitable shape and material, preferably a lightweight, robust material such as plastic or a composite material. In some embodiments the control unit 105 is shaped and dimensioned such that it can fit within the pressure chamber for stowing. For example, in some embodiments, the portable housing is generally cylindrical and approximately 50 cm in length (e.g. 51.1 cm) having an approximately 8.0 cm outer diameter. In addition, in some embodiments the portable housing 905 includes grip features 910, e.g. surface unevenness in designated areas, to provide a good grip when holding the device. Additionally, some embodiments can include brackets or other mounting means for mounting the control unit near the patient, e.g. to a stretcher.

Figure 10A:
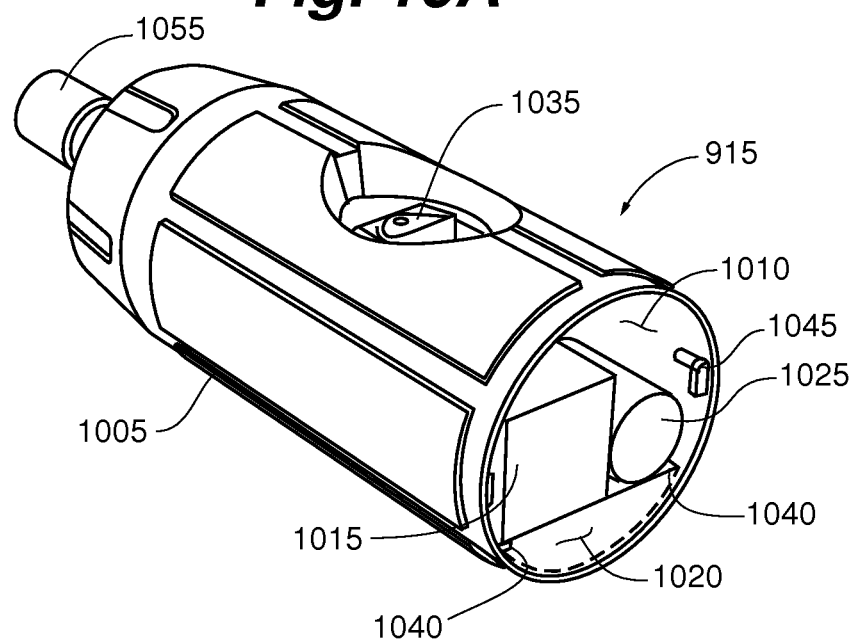
FIG. 10A is a perspective view of a component compartment of a control unit according to some embodiments.
Figure 10B:
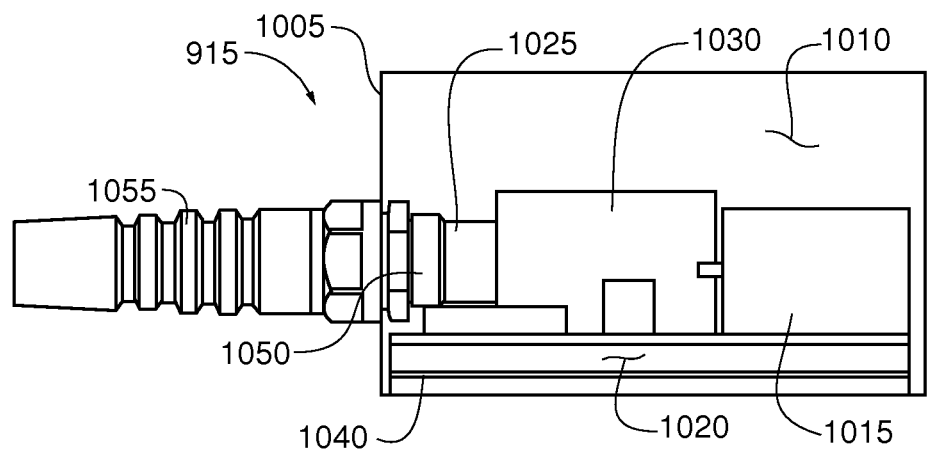
FIG. 10B is a side sectional representation of the component compartment of FIG. 10A.

In some embodiments, the portable housing 905 comprises a component compartment 915 and a power supply compartment 920. FIGS. 10A and 10B show views of a component compartment 915 according to some embodiments of the invention. The component compartment comprises the housing 1005 defining a housing cavity 1010 within which is mounted a pump 1015, internal chamber 1020, valve 1025, printed circuit board 1030, and on/off switch 1035. The pump 1015, valve 1025, and printed circuit board 1030 can be mounted upon a flat upper surface of the internal chamber 1020, which can then be slid into the housing 1005 on rails 1040 which are fastened or molded to the inner wall of the housing 1005. In addition, the component compartment can include a lock mechanism 1045 for releasably connecting with the power supply compartment.

The pump 1015 can comprise any suitable fluid pump capable of generating a pressure up to at least −40 mmHg within the internal chamber 1020. More preferably, the pump 1015 is capable of generating negative pressures greater than −40 mmHg (e.g. −80 mmHg). In some embodiments, the pump 1015 is configured to pump air from the internal chamber 1020 into the housing cavity 1010. In such embodiments, the housing cavity 1010 and internal chamber 1020 correspond to the first and second chambers 830, 835, respectively, of the schematic of FIG. 8. Referring again to FIGS. 10A and 10B, the operation of the pump 1015 can be controlled by a controller located on the printed circuit board 1030. This controller can also interface with the pressure chamber and a temperature sensor therewithin to regulate operation of the pump 1015 and heat transfer element of the pressure chamber.

Valve 1025 is in fluid communication with the internal chamber 1020 and a connector input 1050 connectable with a connector for connecting to a portable pressure chamber. Valve 1025 can be controlled by the controller to connect the internal chamber 1020 with the pressure chamber during negative pressure periods to provide for the introduction of negative pressure to the pressure chamber. In some embodiments the valve 1025 may further be in fluid connection with the housing cavity 1010. Such devices can be described as closed system devices because when generating the negative pressure, the pump 1015 delivers the displaced air from the pressure chamber within the housing cavity 1010 and thus preserves the temperature of the air as modified while within the pressure chamber. During atmospheric pressure periods, such embodiments connect the housing cavity with the pressure chamber to return to the pressure chamber the temperature adjusted air.

Component compartments 915 can further include additional features. For example, in some embodiments, the device further includes a strain relief 1055 for ensuring a proper and enduring connection between the control unit and the connector. Further, the component compartment 915 can include one or more escape valves within an external wall of the housing for connecting one or more of the system chambers to the environment. Such an escape valve can be activated to relieve excess pressure built up within the system during prolonged or normal operation. For example, air leakage into the pressure chamber from the environment when the negative pressure is introduced may remain within the system causing pressure within the pressure chamber (in a closed system) to build up. The escape valve can be triggered by the controller or manually to relieve this excess air. Additionally, in some embodiments, an escape valve can be opened to draw additional environmental air into the system to allow for a more rapid return to atmospheric pressure.

Figure 11:
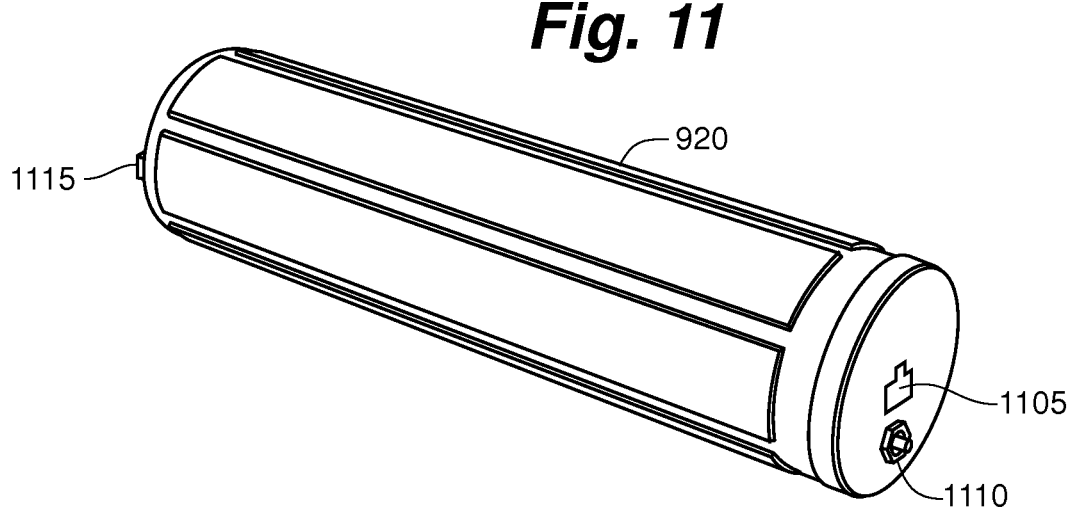
FIG. 11 is a perspective view of a power supply compartment of a control unit according to some embodiments.

An embodiment of a power supply compartment 920 can be seen in FIG. 11. Such a compartment is generally a hollow tube for receiving a power supply or storage device. In some embodiments, the power supply is one or more batteries. The batteries can be rechargeable or disposable, and in some embodiments comprises one or more ANR26650M1 cells available from A123 Systems. Embodiments including rechargeable batteries can further include a charging contact 1105 mounted within the housing of the power supply compartment 920. Additionally, some embodiments may include a fuse 1110 to prevent overcharging of the device. To connect with the component compartment 915, the power supply compartment 920 can include a lock mechanism 1115 which can engage a paired lock mechanism 1045 on the component compartment to lock the two compartments together.

Various embodiments include features for facilitating the transition between pressure periods. For example, the transition from the negative pressure period to the atmospheric pressure period can be accomplished by allowing air to be drawn into the pressure chamber. For example, in some embodiments, the pressure chamber can include an external valve to the environment openable to release the negative pressure (i.e. cause air flow from the relatively higher pressure, atmospheric pressure source to the pressure chamber). Preferably, however, a separate chamber within the control unit or pressure chamber is designated an atmospheric pressure source, thus allowing the device to operate as a closed system device. Most preferably, the device includes a positive pressure chamber, e.g. the first chamber 1210 of the control unit in FIGS. 12A-12D discussed below, which maintains a pressure greater than atmospheric pressure (i.e. a positive pressure) during the negative pressure period. Thus, upon transition from the negative pressure period to the atmospheric pressure period, fluid transfer into the pressure chamber occurs more rapidly due to a greater pressure differential between the positive pressure source and the pressure chamber.

Because of the length of the atmospheric pressure period or the rate at which air can re-enter the pressure chamber, the chamber may not be returned completely to atmospheric pressure between the pulses of negative pressure. In such case, a small amount of negative pressure may remain in the pressure chamber at the end each pulse, i.e. the pressure chamber is returned only to approximately atmospheric pressure. This might be, say, between 0 and −20 mmHg (0 and −2.7 kPa) or more preferably between 0 and −10 mmHg (0 and −1.3 kPa), and more preferably still between 0 and −5 mmHg (0 and −0.67 kPa). Most preferably, the rate at which air can re-enter the pressure chamber and the pulse period are such that the pressure within the chamber is returned to atmospheric pressure during each atmospheric pressure period. Indeed, in the most preferred embodiments, the change in the chamber pressure occurs rapidly such that the time taken to change the pressure is only a small fraction of the atmospheric pressure period, for example, less than 50%, preferably less than 25% and more preferably less than 10% of the atmospheric pressure period. It is most preferred that the plot of pressure against time follows a substantially square-wave plot with sharp transitions at the pressure changes i.e. the change in the chamber pressure is substantially instantaneous. In practice, some rounding of the transitions may occur. Similarly, the control unit should have sufficient capacity to bring the pressure chamber to the desired negative or positive pressure as quickly as possible. In preferred embodiments, the control unit pre-generates the negative pressure prior to the negative pressure period (e.g. during a preceding atmospheric pressure period), so that the transition to the negative pressure period can likewise approach a square wave.

Figure 13:
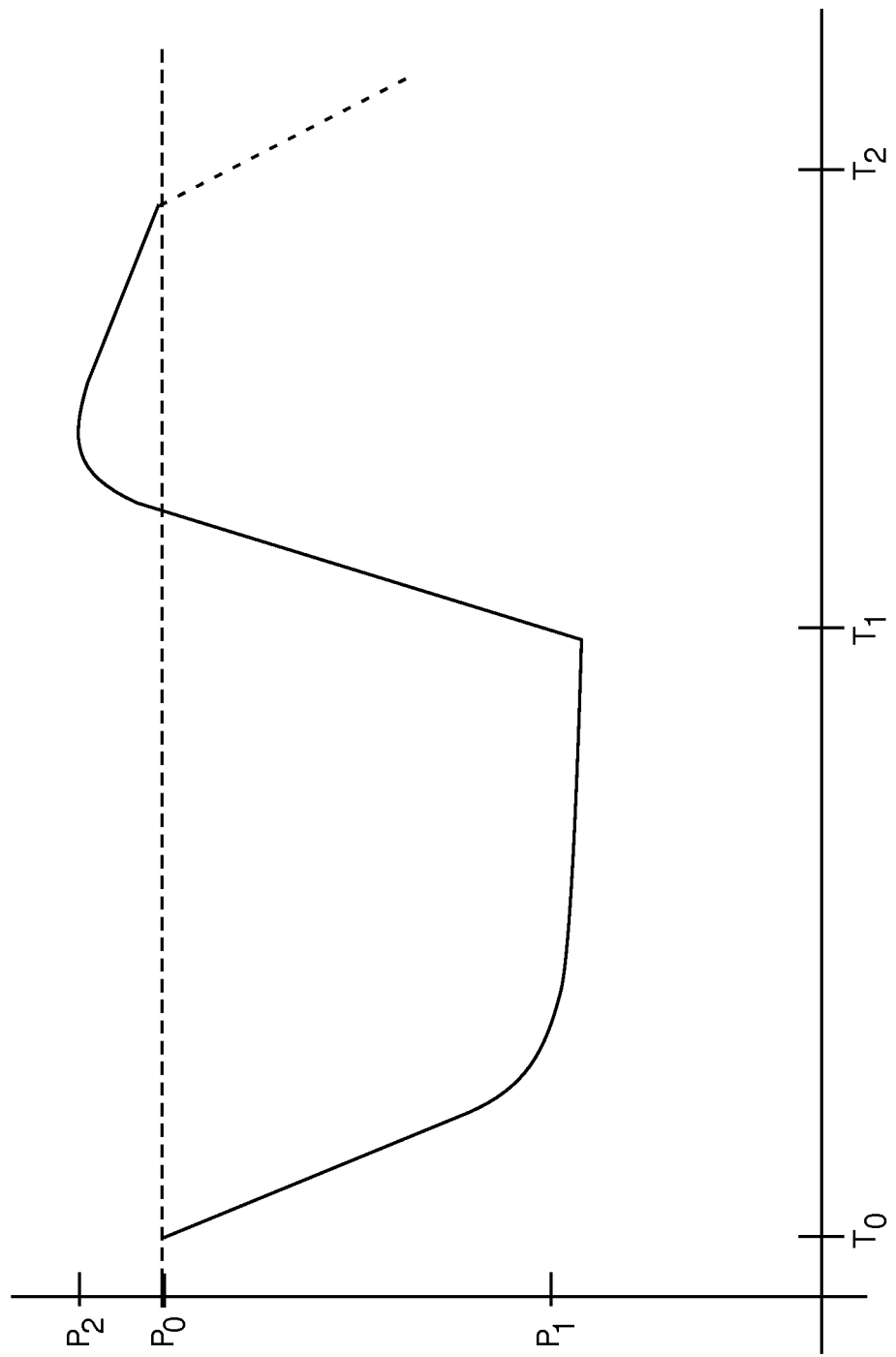
FIG. 13 shows a plot of applied pressure v. time representative of the operation of devices and methods according to some embodiments.

FIG. 13 shows a plot of applied pressure v. time representative of the operation of devices and methods according to some embodiments. This plot represents one cycle of applied pressure within the pressure chamber. Here, the negative pressure period is between $T_0$ and $T_1$, and the atmospheric pressure period is from $T_1$ to $T_2$. In some embodiments, the negative pressure period $T_0$-$T_1$ is approximately 10 seconds in duration, and the atmospheric pressure period $T_1$-$T_2$ is approximately 7 seconds in duration. The transition from atmospheric pressure to negative pressure is indicated at $T_0$ and $T_2$, and the transition from negative pressure to atmospheric pressure is indicated at $T_1$. As described above, in some preferred embodiments, the transition from atmospheric pressure $P_0$ to the negative pressure $P_1$ (i.e. from 0 mmHg to −40 mmHg in some embodiments) is a sharp transition resulting in rapid pressure change, i.e. pressure transition in less than 50% of the duration of the negative pressure period $T_0$-$T_1$. In this embodiment, the transition to the atmospheric pressure period, at $T_1$, results in a pressure $P_2$ greater than atmospheric pressure $P_0$ being applied for a portion or all of the atmospheric pressure period $T_1$-$T_2$. In some embodiments, the application of a positive pressure during the atmospheric pressure period $T_1$-$T_2$ can have certain beneficial effects. For example, the positive pressure $P_2$ exerts force on the patients limb, causing veins to empty faster and further improve circulation. Moreover, positive pressure $P_2$ applied within the pressure chamber gap can press the sleeve and/or heat transfer element against the limb of the patient, improving passive diffusion of heat to or from the limb. Thus, the applied pressure v. time plot of FIG. 13 is representative of the desired operation of some embodiments.

Some embodiments can enhance the in situ or in transit operation of the device by reducing the effect of ambient temperature on the temperature adjustment of the patient. In situations requiring in situ or in transit adjustment of a patient's core body temperature it is often the case that the ambient temperature about the patient is the cause of or contributes to the patient's condition. For instance, an ambient temperature lower than the core body temperature of a hypothermic patient only further contributes to the patient's condition. A closed system device, according to some embodiments, is a device such that substantially all air displaced within the components of the device during introduction of the negative pressure is retained within the device. For example, with reference to FIG. 8, to introduce a negative pressure within the pressure chamber 110, a volume of air can be transferred from the pressure chamber 110 to the control unit 105 (e.g. to the second chamber 835). This volume of air has been temperature adjusted while within the pressure chamber 110 due to the application of the adjustment temperature. During the negative pressure period, this temperature adjusted air can be pumped via pump 810 to first chamber 830. Then, to release the negative pressure from the pressure chamber 110 and return the chamber to atmospheric pressure, substantially the same volume of air can be transferred from the control unit 105 (e.g. first chamber 830) to the pressure chamber 110 rather than drawing ambient temperature, environmental air into the pressure chamber 110. Thus, embodiments of the invention reduce the impact of introducing environmental air into the pressure chamber by recycling the temperature adjusted air within the pressure chamber during successive pressure cycles.

Closed system portable devices can be advantageous for a number of reasons. For example, as described above, the effect of ambient temperature on the temperature adjustment of the patient is reduced. In addition, closed systems can provide for more power efficient devices by reducing the amount of heating or cooling performed by the system. Because the closed system re-circulates temperature adjusted air, the temperature within the pressure chamber can be maintained at the adjustment temperature with less heating or cooling by the heat transfer element. Thus, the work load, and therefore the power draw, of the heat transfer element is reduced. Moreover, the re-circulated, temperature adjusted volume of air can also serve to heat or cool other components within the control unit which can further improve device performance. For example, in some embodiments, batteries used to power the portable device operate more effectively when warmed, so device performance in cool environmental conditions can be improved by providing a closed system.

Figure 12A:
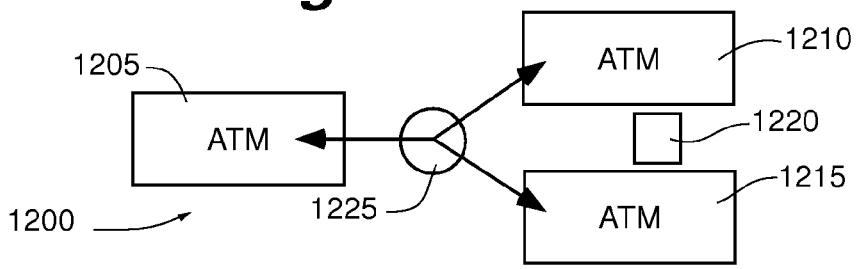
FIGS. 12A-12D show a schematic representation of the operation of the device according to some embodiments.
Figure 12B:
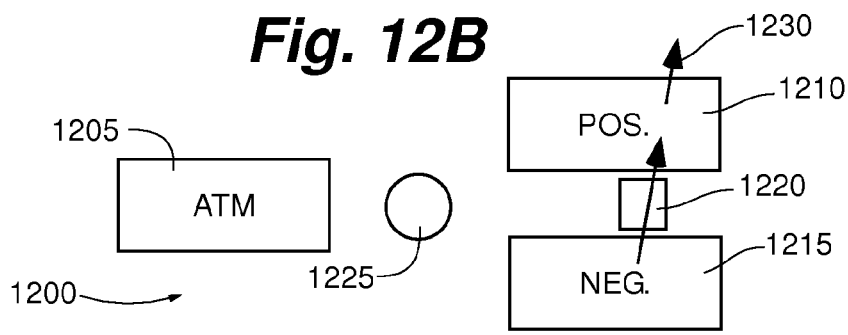

FIGS. 12A-12D show a schematic representation of the operation of an embodiment of the device 1200 providing for substantially square-wave transitions between pressure periods. The shown abstractions of the pressure chamber 1205, first chamber 1210, and second chamber 1215, can correlate, for example, with the pressure chamber 110, first chamber 830, and second chamber 835, of the embodiment shown in FIG. 8. Initially, as shown in FIG. 12A, the pump 1220 is off, and valve 1225 is open allowing fluid communication between each of the pressure chamber 1205, first chamber 1210, and second chamber 1215 each chamber being at approximately atmospheric pressure. When the device is actuated, as shown in FIG. 12B, valve 1225 is closed and the pump 1220 is turned on. While on, the pump displaces air from the second chamber 1215 and into the first chamber 1210, thus causing a negative pressure to build up in the second chamber 1215 while increasing the pressure within the first chamber 1210. The pressure within the pressure chamber 1205 remains at approximately atmospheric pressure. In some embodiments, an escape valve 1230 may be opened to release some air from the first chamber 1210 during the initial building of a negative pressure within the second chamber 1215. In addition, the negative pressure built up within the second chamber may be greater than (i.e. more negative than) the desired negative pressure to be applied within the pressure chamber.

Figure 12C:
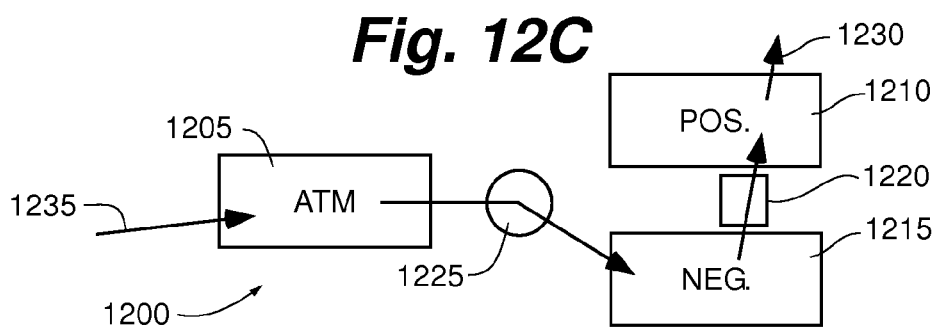

Next, as shown in FIG. 12C representing the device state during the negative pressure period referenced above, the valve connects the second chamber 1215 with the pressure chamber 1205 causing air to flow from the pressure chamber 1205 to the second chamber 1215 and the pressures within each of these chambers to equalize. Pump 1220 remains on as necessary to draw the pressure within the pressure chamber towards the desired negative pressure, and maintain it at that level. Air pumped from the second chamber 1215 is delivered to the first chamber causing the first chamber to maintain a positive pressure relative to the pressure chamber 1205 and, in some embodiments, atmospheric pressure. In some embodiments, excess air may leak 1235 into the system, e.g.

at an imperfect seal of the pressure chamber 1205. Over time, this extra volume of air could cause excess pressure to build within the system, namely within the first chamber 1210 during the negative pressure period. Thus, in some embodiments, an escape valve 1230 connected with the first chamber 1210 or elsewhere within the system can be opened to allow excess air to escape the system.

Figure 12D:
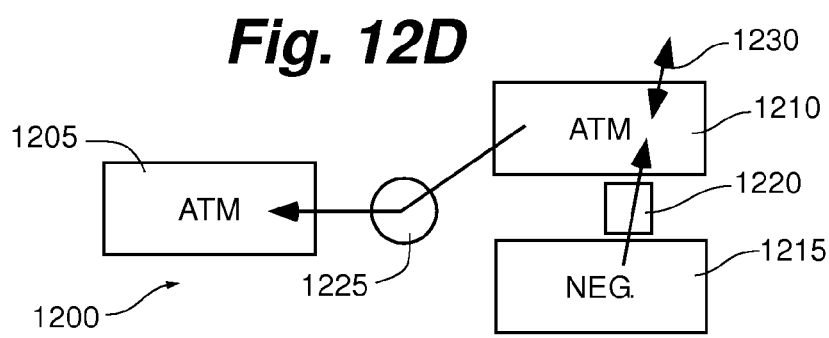

FIG. 12D represents the device state during the atmospheric pressure period referenced above. During this period, the valve 1225 switches to connect the first chamber 1210 with the pressure chamber 1205. With this connection in place, air flows from the first chamber 1210 to the pressure chamber 1205 and the pressure chamber is restored to approximately atmospheric temperature. An escape valve coupled with the first chamber 1210 can be opened as necessary to during this period to allow the first chamber and pressure chamber to equalize at approximately atmospheric temperature. Additionally, during the atmospheric pressure period, pump 1220 remains on as necessary to accumulate negative pressure within the second chamber 1215. As above, this negative pressure may be greater than the desired negative pressure to be applied within the pressure chamber.

As described with reference to FIGS. 12A-12D above, some embodiments of the invention introduce a negative pressure to the pressure chamber only after the negative pressure has been pre-accumulated within another chamber of the device. Such operation is preferred because it provides for sharper transitions from the positive pressure period to the negative pressure period. Additionally, by allowing a positive pressure to build within the first chamber prior to the positive pressure period, the transition time from the negative pressure period to the positive pressure period is reduced. Thus, some embodiments can provide the substantially square-wave operation.

Another advantage of devices providing for operation according to embodiments of FIGS. 12A-12D is that they provide for closed system operation. As described above, closed system devices can reduce the effect of the ambient temperature on the temperature adjustment of the patient and increase the power efficiency of the device. The term "closed system," as used herein refers to a device where substantially all air displaced within the system during generation of the negative pressure is retained within the device. While closed system devices capable of substantially instantaneous pressure changes are preferred, this disclosure should not be read to exclude embodiments which do not provide for square-wave and closed system operation with regard to the pressure changes within the device. For example, in some devices, negative pressure can be introduced by removing air directly from the pressure chamber. Moreover, negative pressure can be released by opening a valve to connect the pressure chamber with the environment.

In another aspect, embodiments of the invention provide methods for the in situ or in transit adjustment of a patient's core body temperature. In one such method, a limb of the patient is installed with a sleeve comprising an absorbent material. Either before installing the sleeve about the limb or after the sleeve has been installed, the sleeve is wetted with a liquid. The limb having the wetted sleeve installed thereon is inserted into a pressure chamber such that the limb is substantially sealed from external conditions. The pressure chamber can be any pressure chamber described herein, and generally comprises a substantially rigid casing and a heating/cooling element within the casing. Substantially all liquid in the interior of the pressure chamber can be carried by the sleeve. Depending upon the application, the heating/cooling element is activated to either (a) increase the temperature within the pressure chamber to a heating temperature or (b) decrease the temperature within the pressure chamber to a cooling temperature. Negative pressure is alternatingly introduced to the pressure chamber and released from the pressure chamber, such that when the negative pressure is released from the pressure chamber, the pressure chamber is at approximately atmospheric pressure. In some preferred embodiments, the step of alternatingly introducing a negative pressure to the chamber can be a closed system process accomplished as described above.

In such a method, the wetting of the sleeve can be accomplished in a number of ways that lend to the in situ or in transit use of the method. For example, in some embodiments, the sleeve can be wetted by submerging the limb having the sleeve installed thereon within a volume of the liquid. For example, in some embodiments the pressure chamber can be filled or partially filled with a liquid, and a limb having the thermal transfer sleeve installed thereon can be inserted into the pressure chamber. In such case, a volume of the liquid may be displaced from the pressure chamber, while a large portion of the liquid is absorbed by the thermal transfer sleeve. Any excess liquid within the chamber can then be emptied out. Alternatively, a volume of the liquid can be poured over a limb having the sleeve installed thereon. Further still, some embodiments can include a channel or inlet within an exterior surface of the pressure chamber through which the liquid can be supplied. In such embodiments, the limb having the sleeve installed thereon can be inserted into the dry pressure chamber, and the liquid can then be delivered into the device through the channel or inlet. In each case, the liquid can be selected from generally any available source, for example, a canteen of drinking water or liquid from a nearby river, pond, or other natural water source. In another aspect, some embodiments include the installation of a pre-wet thermal transfer sleeve. If a pre-wet sleeve is used the step of wetting the sleeve includes removing the pre-wet sleeve from its packaging prior to installation. Thus, with such sleeves, no additional liquid source is necessary at the locale of use.

In some embodiments, the step of installing the sleeve about the limb and wetting the sleeve further comprise the step of ensuring that the thermal transfer sleeve is in skin tight contact about the limb. As described above, in some embodiments, it is desirable for the thermal transfer sleeve to contact the limb such that air gaps between the sleeve and limb are minimized to improve thermal and pressure transfer from the pressure chamber to the limb. To ensure the sleeve is in skin tight contact about the limb, a user or the patient can start at the distal end of the limb and press the sleeve against the limb, working back toward the open proximal end. Such a method can further operate to remove excess liquid from the thermal transfer sleeve.

In some embodiments, methods according to the present invention further include preparing the limb for installation. For example, in embodiments which include anatomical features, e.g. a wrist feature, it can often be difficult to properly insert a patient's limb into the pressure chamber. This is because a narrow portion of the chamber created by the inclusion of the anatomical feature can impede the limb's path into the chamber. In cases where methods and devices according to embodiments of the invention are being installed upon an unconscious patient, inserting the limb into the chamber can be especially difficult and improper installation can result in injury to the patient. Thus, preparing the limb for insertion into the pressure chamber can include the step of straightening the limb or ensuring that the limb is straightened prior to insertion. For example, where the limb is an arm and the pressure chamber includes a wrist portion, preparing the limb for installation can include straightening the fingers to provide a minimal cross-sectional size for insertion of the hand beyond the wrist portion and to reduce the incidence of injury to the patient. Moreover, in some embodiments insertion into the chamber can be facilitated by temporarily expanding the pressure chamber. Such methods are preferable where the pressure chamber is an expandable pressure chamber such as those described above with reference to FIGS. 5A-5C.

Methods according to embodiments of the invention can be especially useful for in situ or in transit adjustment of a patient's core body temperature. To facilitate such use, the method can include the step of transporting a system or device according to any of the embodiments discussed above to the location of a patient in need of temperature adjustment. Such a method can be especially useful where the patient is immobile or unconscious. To deliver the device to the patient, the device can be hand-carried or connected with a vehicle such as, e.g. an ambulance. Preferably, the device can be hand-carried within a carrying case. Upon reaching the patient, the portable device can be removed from the carrying case. In some embodiments, it may be necessary to ensure that the control unit is in fluid connection with the pressure chamber. If not, the pressure chamber should be connected with the control unit either directly or, preferably, with a connector. In some instances, it is important to ensure that the limb is substantially sealed from external conditions. For example, where the device has been brought to a hypothermic patient in a cold environment, ensuring that the limb is substantially sealed from the cold external environment can enhance operation of the device and method. Then the remainder of the steps for using the device can be carried out in the location of the patient (in situ) or as the patient is being transported (in transit).

Moreover, it should be recognized that devices and methods according to some embodiments can be used in manners different from those described above to accomplish some of the functionality described above. For example, embodiments of the devices described above can be used to heat or cool a patient without the application of a pulsating pressure. In such case, the heat transfer element (alone or with the thermal transfer sleeve) can be used to heat or cool a limb inserted into a pressure chamber without the application of pressure or with a constant pressure applied within the chamber. Although generally less effective, in most cases, than the uses described above such alternative use may provide for in situ or in transit heating or cooling of a patient if, for example, the pump of the device were to break. Likewise, embodiments of devices and methods can be used to apply a pressure or pulsating pressure to the limb of a patient without the application of a heating or cooling temperature. Accordingly, the device can be used to increase blood flow within a limb of a patient who does not require temperature adjustment.

Although the present invention has been described in considerable detail with reference to certain disclosed embodiments, the disclosed embodiments have been presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A device comprising:
    a pressure chamber that includes a seal element and a casing, the casing defining a pressure controlled environment and being configured to expand open to facilitate installation of a limb of a patient in the casing, the pressure chamber comprising an elastic shell fitted about an exterior surface of the casing that is configured to bias the casing closed during operation of the pressure chamber yet stretch to allow for expansion of the casing to facilitate insertion or removal of the limb from the casing, the seal element configured to seal the pressure chamber about the limb; and
    a control unit connectable to the pressure chamber and adapted, when connected to the pressure chamber, to alternatingly introduce a negative pressure to the pressure chamber during a negative pressure period and release the negative pressure from the pressure chamber to restore the pressure chamber to approximately atmospheric pressure during an atmospheric pressure period.

2. The device of claim 1, wherein the device is configured to fit within a carrying cases such that the device and carrying case are configured to be manually carried by an individual.

3. The device of claim 1, wherein the limb comprises at least one of an arm or a leg.

4. The device of claim 3, wherein the limb is an arm.

5. The device of claim 1, wherein the control unit and pressure chamber when connected, comprise a substantially closed system in that (a) introducing the negative pressure to the pressure chamber comprises transferring an amount of air from the pressure chamber to the control unit and (b) releasing the negative pressure from the pressure chamber comprises transferring substantially the same amount of air from the control unit to the pressure chamber.

6. The device of claim 1, wherein the pressure chamber is tubular shaped and defines a circular or oval cross-section.

7. The device of claim 1, wherein the pressure chamber comprises an anatomical feature configured to conform to the limb.

8. The device of claim 7, wherein the anatomical feature is configured to conform to an arm.

9. The device of claim 7, wherein the casing includes a narrower wrist portion between a comparatively wider forearm portion and a hand portion.

10. The device of claim 1, wherein the elastic shell comprises Neoprene.

11. The device of claim 1, wherein the casing comprises a hinged edge and an opposed openable edge.

12. The device of claim 1, wherein the casing is configured to expand by pivoting a top half of the casing relative to a bottom half of the casing.

13. The device of claim 1, wherein the negative pressure period is between 5 seconds and 15 seconds and the atmospheric pressure period is different than the negative pressure period.

14. The device of claim 1, wherein the negative pressure is between −20 mmHg and −80 mmHg (−2.7 kPa and −10.7 kPa).

15. The method of claim 14, wherein inserting the limb comprises inserting the arm.

16. The device of claim 1, wherein the casing is a substantially rigid casing.

17. A method comprising:
    providing a pressure chamber that includes a seal element and a casing, the casing defining a pressure control led environment and being configured to expand open to facilitate installation of a limb of a patient in the casing, the pressure chamber comprising an elastic shell fitted about an exterior surface of the casing that is configured to bias the casing closed during operation of the pressure chamber yet stretch to allow for expansion of the casing to facilitate insertion or removal of the limb from the casing, the seal element configured to seal the pressure chamber about the limb;

inserting the limb of the patient in the pressure chamber by at least expanding the casing open, installing the limb in the casing, and biasing the casing closed so as to seal the limb from external conditions; and increasing blood flow to an area of skin of the limb within the pressure chamber by at least (i) generating a negative pressure within the pressure chamber for a first time interval and (ii) releasing the negative pressure within the pressure chamber for a second time interval that is different than the first time interval.

18. The method of claim 17, wherein generating the negative pressure within the pressure chamber comprises generating the negative pressure for approximately 10 seconds.

19. The method of claim 17, wherein releasing the negative pressure comprises releasing the negative pressure for approximately 7 seconds.

20. The method of claim 17, wherein generating the negative pressure in the pressure chamber comprises generating the negative pressure for between 5 seconds and 15 seconds and releasing the negative pressure comprises releasing the negative pressure for between 2 seconds and 15 seconds.

21. The method of claim 17, wherein the negative pressure is between −20 mmHg and −80 mmHg (−2.7 kPa and −10.7 kPa).

22. The method of claim 21, wherein the negative pressure is −40 mmHg (−5.3 kPa).

23. The method of claim 17, wherein the casing is a substantially rigid casing.

24. The method of claim 17, wherein inserting the limb comprises inserting at least one of an arm or a leg.

25. The method of claim 17, wherein the pressure chamber is tubular shaped and defines a circular or oval cross-section.

26. The method of claim 17, wherein the pressure chamber comprises an anatomical feature configured to conform to the limb.

27. The method of claim 26, wherein the anatomical feature is configured to conform to an arm.

28. The method of claim 26, wherein the casing includes a narrower wrist portion between a comparatively wider forearm portion and a hand portion.

29. The method of claim 17, wherein the elastic shell comprises Neoprene.

30. The method of claim 17, wherein the casing comprises a hinged edge and opposed openable edge.

31. The method of claim 17, wherein inserting the limb comprises pivoting a top half of the casing relative to a bottom half of the casing.

* * * * *